US011494899B2

(12) United States Patent
Joyce et al.

(10) Patent No.: US 11,494,899 B2
(45) Date of Patent: Nov. 8, 2022

(54) APPARATUS AND METHOD FOR OPERATING A PERSONAL GROOMING APPLIANCE OR HOUSEHOLD CLEANING APPLIANCE

(71) Applicant: The Procter & Gamble Company, Cincinnati, OH (US)

(72) Inventors: Jonathan Livingston Joyce, Independence, KY (US); Faiz Feisal Sherman, Mason, OH (US); Xiaole Mao, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 413 days.

(21) Appl. No.: 16/708,496

(22) Filed: Dec. 10, 2019

(65) Prior Publication Data

US 2020/0201266 A1    Jun. 25, 2020

Related U.S. Application Data

(60) Provisional application No. 62/783,929, filed on Dec. 21, 2018.

(51) Int. Cl.
| *G05B 13/02* | (2006.01) |
| *A46B 13/02* | (2006.01) |

(Continued)

(52) U.S. Cl.
CPC ............ *G06T 7/0012* (2013.01); *A46B 13/02* (2013.01); *A46B 15/0004* (2013.01);
(Continued)

(58) Field of Classification Search
CPC ... A46B 13/02; A46B 15/0004; A47L 9/2826; A47L 2201/04; A47L 2201/06;
(Continued)

(56) References Cited

U.S. PATENT DOCUMENTS

| 5,880,962 A | 3/1999 | Andersson |
| 5,951,498 A | 9/1999 | Arnett |

(Continued)

FOREIGN PATENT DOCUMENTS

| AU | 680538 B2 | 7/1997 |
| CN | 101450010 A | 6/2009 |

(Continued)

OTHER PUBLICATIONS

All Office Actions; U.S. Appl. No. 16/708,489.

(Continued)

*Primary Examiner* — Marc Carlson
(74) *Attorney, Agent, or Firm* — Steven Robert Chuey; Sarah M DeCristofaro

(57) ABSTRACT

A system and method for operating a household cleaning appliance, including: providing a household cleaning appliance including, a powered and electronically controlled cleaning implement, and at least one physical sensor taken from a group consisting of: an orientation sensor, an acceleration sensor, an inertial sensor, a global positioning sensor, a pressure sensor, a load sensor, audio sensor, humidity sensor, and a temperature sensor; providing a camera associated with the household cleaning appliance; deriving an augmented classification using one or more classifiers classifying the physical sensor data and the image data; and modifying operation of the cleaning implement based upon the augmented classification.

15 Claims, 16 Drawing Sheets

(51) Int. Cl.

| | |
|---|---|
| *A46B 15/00* | (2006.01) |
| *G09B 19/00* | (2006.01) |
| *A47L 9/28* | (2006.01) |
| *G06T 7/00* | (2017.01) |
| *A61B 5/00* | (2006.01) |
| *G06K 9/62* | (2022.01) |
| *G06N 3/08* | (2006.01) |
| *G06Q 30/06* | (2012.01) |
| *G06N 20/00* | (2019.01) |
| *G05B 15/02* | (2006.01) |
| *G06N 5/04* | (2006.01) |
| *A61C 17/22* | (2006.01) |

(52) U.S. Cl.
CPC .......... *A47L 9/2826* (2013.01); *A61B 5/0077* (2013.01); *A61B 5/0088* (2013.01); *G05B 13/0265* (2013.01); *G05B 15/02* (2013.01); *G06K 9/628* (2013.01); *G06K 9/6256* (2013.01); *G06N 3/08* (2013.01); *G06N 5/04* (2013.01); *G06N 20/00* (2019.01); *G06Q 30/0631* (2013.01); *G09B 19/0084* (2013.01); *A47L 2201/04* (2013.01); *A47L 2201/06* (2013.01); *A61C 17/221* (2013.01); *G06K 9/6262* (2013.01); *G06T 2207/20081* (2013.01); *G06T 2207/30036* (2013.01); *G06T 2207/30088* (2013.01); *G06T 2207/30201* (2013.01)

(58) Field of Classification Search
CPC ............ G05B 13/0265; G05B 15/02; G09B 19/0084; A61B 5/0077; A61B 5/0088; G06T 7/0012; G06T 2207/20081; G06T 2207/30036; G06T 2207/30088; G06T 2207/30201; G06K 9/6256; G06K 9/628; G06K 9/6262; G06N 3/08; G06N 5/04; G06N 20/00; G06Q 30/0631; A61C 17/221
See application file for complete search history.

(56) References Cited

U.S. PATENT DOCUMENTS

| | | | |
|---|---|---|---|
| 5,975,893 A | 11/1999 | Chishti | |
| 6,328,567 B1 | 12/2001 | Morris | |
| 6,532,299 B1 | 3/2003 | Sachdeva | |
| 6,560,027 B2 | 5/2003 | Meine | |
| 6,648,640 B2 | 11/2003 | Rubbert | |
| 6,739,869 B1 | 5/2004 | Taub | |
| 6,786,732 B2 | 9/2004 | Savill | |
| 6,793,489 B2 | 9/2004 | Morris | |
| 7,234,936 B2 | 6/2007 | Lai | |
| 7,309,232 B2 | 12/2007 | Rutherford | |
| 7,935,065 B2 | 5/2011 | Martin | |
| 7,987,099 B2 | 7/2011 | Kuo | |
| 8,073,212 B2 | 12/2011 | Gerlach | |
| 8,161,792 B2 | 4/2012 | Schlueter | |
| 8,203,713 B2 | 6/2012 | Ramirez | |
| 8,306,608 B2 | 11/2012 | Mandelis | |
| 8,372,020 B2 | 2/2013 | Martin | |
| 8,381,571 B2 | 2/2013 | Wilhelm | |
| 8,647,119 B1 | 2/2014 | Nagai | |
| 8,744,192 B2 | 6/2014 | Ortins | |
| 8,832,019 B2 | 9/2014 | Gao | |
| 9,020,236 B2 | 4/2015 | Wang | |
| 9,079,030 B2 | 7/2015 | Holloway | |
| 9,107,722 B2 | 8/2015 | Matov | |
| 9,271,808 B2 | 3/2016 | Teixeira | |
| 9,308,064 B2 | 4/2016 | Binner | |
| 9,452,037 B2 | 9/2016 | Edwards | |
| 9,480,539 B2 | 11/2016 | Ortlieb | |
| 9,492,245 B2 | 11/2016 | Sherwood | |
| 9,510,757 B2 | 12/2016 | Kopelman | |
| 9,626,462 B2 | 4/2017 | Somasundaram | |
| 9,693,845 B2 | 7/2017 | Price | |
| 9,737,257 B2 | 8/2017 | Ribnick | |
| 9,757,020 B1 | 9/2017 | Elazar | |
| 9,770,217 B2 | 9/2017 | Sandholm | |
| 9,775,504 B1 | 10/2017 | Elazar | |
| 9,788,917 B2 | 10/2017 | Mah | |
| 9,805,167 B2 | 10/2017 | Van Lierde | |
| 10,482,522 B2 | 11/2019 | Robinson et al. | |
| 10,647,011 B2 | 5/2020 | Robinson et al. | |
| 10,751,892 B2 | 8/2020 | Godlieb et al. | |
| 11,278,384 B2 | 3/2022 | Serval et al. | |
| 2006/0099545 A1 | 5/2006 | Lai | |
| 2007/0003900 A1 | 1/2007 | Miller | |
| 2008/0209650 A1 | 9/2008 | Brewer | |
| 2009/0092955 A1 | 4/2009 | Hwang | |
| 2009/0177495 A1 | 7/2009 | Abousy | |
| 2009/0317770 A1 | 12/2009 | Gatzemeyer et al. | |
| 2010/0069083 A1 | 3/2010 | Wei | |
| 2010/0281636 A1 | 11/2010 | Ortins | |
| 2011/0159460 A1 | 6/2011 | Miller | |
| 2011/0208537 A1 | 8/2011 | Sachdeva | |
| 2012/0151697 A1 | 6/2012 | Farrell et al. | |
| 2012/0189976 A1 | 7/2012 | Mcdonough | |
| 2013/0232717 A1* | 9/2013 | Lee .................. G08B 13/19613 901/1 |
| 2014/0030674 A1 | 1/2014 | Nguyen | |
| 2014/0096331 A1 | 4/2014 | Farrell | |
| 2014/0229145 A1 | 8/2014 | Van Lierde | |
| 2015/0044629 A1 | 2/2015 | Wang | |
| 2015/0169845 A1 | 6/2015 | Bradley | |
| 2015/0319326 A1 | 11/2015 | Pfeiffer | |
| 2016/0038092 A1 | 2/2016 | Golay | |
| 2016/0070821 A1 | 3/2016 | Somasundaram | |
| 2016/0143718 A1 | 5/2016 | Serval | |
| 2016/0167241 A1 | 6/2016 | Goldfarb et al. | |
| 2016/0175068 A1 | 6/2016 | Cai | |
| 2016/0235357 A1 | 8/2016 | Ohmer | |
| 2016/0256035 A1 | 9/2016 | Kopelman | |
| 2017/0076443 A1 | 3/2017 | Ye | |
| 2017/0100208 A1 | 4/2017 | Wen | |
| 2017/0169562 A1 | 6/2017 | Somasundaram | |
| 2017/0172418 A1 | 6/2017 | Munro | |
| 2017/0238692 A1 | 8/2017 | Sarubbo | |
| 2017/0304024 A1 | 10/2017 | Nóbrega | |
| 2017/0325647 A1* | 11/2017 | Kwak .................. A47L 9/009 |
| 2017/0340419 A1 | 11/2017 | Ohtake | |
| 2017/0345147 A1 | 11/2017 | Ohtake | |
| 2018/0132602 A1 | 5/2018 | Gatzemeyer | |
| 2019/0343354 A1* | 11/2019 | Hong .................. G06N 20/00 |
| 2020/0179089 A1 | 6/2020 | Serval et al. | |
| 2020/0201272 A1 | 6/2020 | Joyce et al. | |
| 2020/0202520 A1 | 6/2020 | Joyce et al. | |
| 2020/0202521 A1 | 6/2020 | Joyce et al. | |
| 2020/0345190 A1* | 11/2020 | Buehler ................ A47L 9/2847 |

FOREIGN PATENT DOCUMENTS

| | | | |
|---|---|---|---|
| CN | 101791253 B | 12/2014 | |
| CN | 205494064 U | 8/2016 | |
| CN | 105919684 A | 9/2016 | |
| CN | 106333480 A | 1/2017 | |
| CN | 106725957 A | 5/2017 | |
| EP | 2637073 A2 * | 9/2013 | ............ A47L 9/009 |
| WO | WO2006137661 A1 | 12/2006 | |
| WO | WO2013001462 A3 | 5/2013 | |
| WO | WO2014016718 A1 | 1/2014 | |
| WO | WO2016082784 A1 | 6/2016 | |
| WO | WO2016127250 A1 | 8/2016 | |
| WO | WO2016180929 A1 | 11/2016 | |
| WO | WO2017073986 A1 | 5/2017 | |
| WO | WO2017094004 A1 | 6/2017 | |
| WO | WO2017115200 A1 | 7/2017 | |
| WO | WO2017145033 A1 | 8/2017 | |
| WO | WO2017157411 A1 | 9/2017 | |
| WO | WO2017218040 A1 | 12/2017 | |

(56) References Cited

FOREIGN PATENT DOCUMENTS

| WO | WO2017218951 A1 | 12/2017 |
|---|---|---|
| WO | WO2017220619 A1 | 12/2017 |
| WO | 2018087627 A1 | 5/2018 |

OTHER PUBLICATIONS

All Office Actions; U.S. Appl. No. 16/708,490.
Ail Office Actions; U.S. Appl. No. 16/708,491.
"Method and System for MeasuringEffectiveness of Tooth Brushing", ip.com Journal, ip.com Inc., Westhenrietta, NY, US,Dec. 6, 2018 (Dec. 6, 2018), XP013181263,ISSN: 1533-0001p. 1, paragraph 1—p. 2, paragraph 4.
International Search Report and Written Opinion; Application Ser. No. PCT/US2019/065323; dated Apr. 3, 2020, 14 pages.
International Search Report and Written Opinion; Application Ser. No. PCT/US2019/065320; dated Jun. 23, 2020, 19 pages.
International Search Report and Written Opinion; Application Ser. No. PCT/US2019/065322; dated Apr. 3, 2019, 14 pages.
International Search Report and Written Opinion; Application Ser. No. PCT/US2019/065321; dated Apr. 7, 2020, 14 pages.
Takuma Yoshitani et al: "Iumio", Pervasive and Ubiquitous Computing, ACM, 2PENN Plaza, Suite 701 New York NY10121-0701 USA,Sep. 12, 2016 (Sep. 12, 2016), pp. 605-615, XP058279124,DOI: 10.1145/2971648.2971704ISBN: 978-1-4503-4461-6figures 1,2,3,7p. 605, col. 2—p. 611, col. 2.
U.S. Appl. No. 16/708,489, filed Dec. 10, 2019, Jonathan Livingston Joyce et al.
U.S. Appl. No. 16/708,490, filed Dec. 10, 2019, Jonathan Livingston Joyce et al.
U.S. Appl. No. 16/708,491, filed Dec. 10, 2019, Jonathan Livingston Joyce et al.
Nathan et al., "A Survey on Smart Homes for Aging in Place: Toward Solutions to the Specific Needs of the Elderly", IEEE Signal Processing Magazine, vol. 35, Issue: 5, Sep. 2018, pp. 111-119.
Pirzada et al., "Sensors in Smart Homes for Independent Living of the Elderly", 5th International Multi-Topic ICT Conference, Apr. 25-27, 2018, pp. 1-8.
Rashidi et al., "A Survey on Ambient-Assisted Living Tools for Older Adults", IEEE Journal of Biomedical and Health Informatics, vol. 17, Issue: 3, May 2013, pp. 579-590.
Suryadevara et al., "Wireless sensors network based safe home to care elderly people: A realistic approach", IEEE Recent Advances in Intelligent Computational Systems, Sep. 22-24, 2011, pp. 1-5.

\* cited by examiner discriminating between two or more motion patterns ($15_1$, $15_2$, $15_3$, ..., $15_n$) contained in a set (15) of motion patterns of the movable treatment device (11)

— 801 receiving at least one inertial sensor data ($17_1$) from the inertial sensor (13), the at least one inertial sensor data ($17_1$) representing a movement of the movable treatment device (11)

— 802 receiving and processing by means of a neural network (18) the at least one inertial sensor data ($17_1$) and mapping the at least one inertial sensor data ($17_1$) to at least one motion pattern ($15_1$, $15_2$, $15_3$, ..., $15_n$) contained in the set (15) of motion patterns, wherein said motion patterns ($15_1$, $15_2$, $15_3$, ..., $15_n$) contained in the set (15) of motion patterns are each associated with one or more different zones ($21_1$, $21_2$, $21_3$, ..., $21_n$) of the target surface (12) so that the mapping of the at least one inertial sensor data ($17_1$) with the at least one motion pattern ($15_1$, $15_2$, $15_3$, ..., $15_n$) indicates an estimation of the location of the movable treatment device (11) with respect to the one or more zones ($21_1$, $21_2$, $21_3$, ..., $21_n$) of the target surface (12)

— 803

FIG. 8 discriminating between two or more motion patterns ($15_1$, $15_2$, $15_3$, ..., $15_n$) contained in a set (15) of motion patterns of the movable personal appliance (11)

— 1201 providing at least one inertial sensor data $17_1$, $17_2$, $17_3$, ..., $17_n$ from the inertial sensor 13 to the motion pattern recognition device 14, the at least one inertial sensor data $17_1$, $17_2$, $17_3$, ..., $17_n$ representing a motion of the movable personal appliance 11.

— 1202 receiving and processing, by means of a neural network 18, the at least one inertial sensor data $17_1$, $17_2$, $17_3$, ..., $17_n$ and mapping the at least one inertial sensor data $17_1$, $17_2$, $17_3$, ..., $17_n$ to at least one motion pattern $15_1$, $15_2$, $15_3$, ..., $15_n$ contained in the set 15 of motion patterns, wherein the at least one mapped motion patterns $15_1$, $15_2$, $15_3$, ..., $15_n$ is associated with at least one class member 101A, 101B, 102A, 102B, ..., nA, nB of at least one class 101, 102, 103, 104 so that the at least one class member 101A, 101B, 102A, 102B, ..., nA, nB is selected based on the motion of the movable personal appliance 11

APPARATUS AND METHOD FOR OPERATING A PERSONAL GROOMING APPLIANCE OR HOUSEHOLD CLEANING APPLIANCE

BACKGROUND

There is a need for an ability for "smart" grooming or household appliances and associated systems to leverage the use of combinations of internal sensor data and image data to improve the user's experience related to the grooming or household appliance.

SUMMARY

A first aspect of the current disclosure provide a system and method for operating a personal grooming/household appliance that includes: providing a personal grooming/household appliance including (a) a powered and electronically controlled grooming/cleaning implement, and (b) at least one physical sensor taken from a group consisting of: an orientation sensor, an acceleration sensor, an inertial sensor, a global positioning sensor, a pressure sensor, a load sensor, audio sensor, magnetic sensor, humidity sensor, and a temperature sensor; providing a camera associated with the personal grooming/household appliance; deriving an augmented classification using one or more classifiers classifying the physical sensor data and the image data; and modifying operation of the grooming/household appliance or implement based upon the augmented classification.

In a detailed embodiment, the camera is located on the personal grooming/household appliance.

Alternately, or in addition, the personal grooming/household appliance further includes a computer network interface transmitting and receiving data over a computer network and the camera is located on a computerized device that includes a computer network interface at least transmitting image data over the computer network. In a further detailed embodiment, the operation modifying step is further based upon a treatment plan implemented by a software application operating, at least in part, on the computerized device. In a further detailed embodiment, the treatment plan is customized for a user of the grooming appliance. Alternatively, or in addition, the augmented classification is reconciled against the treatment plan to determine treatment progress with respect to the treatment plan. Alternatively, or in addition, the augmented classification is used, at least in part, to establish the treatment plan.

In another detailed embodiment of the first aspect, the step of deriving the augmented classification is performed by a single classifier. Alternatively, the method includes classifying sensor data received from the physical sensor using a trained machine learning classifier to generate a physical classification; and classifying image data received from the camera using a trained machine learning classifier to generate an image classification; where the step of deriving the augmented classification is based upon the combination of the physical classification and the image classification.

In another detailed embodiment of the first aspect, the appliance is a dental appliance; the grooming implement is a brush, a fluid nozzle and/or a flossing tape; and the augmented classification pertains to the position of the grooming implement with respect to a user's mouth. In a further detailed embodiment, the modifying operation step deactivates the grooming implement when the augmented classification indicates that the grooming implement is outside of the user's mouth. Alternatively, or in addition, the grooming implement is a motorized brush and the modifying operation adjusts a brush speed setting based upon the position of the grooming implement with respect to the user's mouth as indicated, at least in part, by the augmented classification.

In another detailed embodiment of the first aspect, the augmented classification pertains, at least in part, to whether or not the grooming/cleaning implement is being implemented, and the step of modifying operation updates a maintenance setting based upon an amount of time that the grooming/cleaning implement is being implemented.

In another detailed embodiment of the first aspect, the augmented classification pertains, at least in part, to the position of the grooming implement with respect to a user's body part, and the step of modifying operation modifies operation of the grooming implement, based at least in part, upon the position of the of the grooming implement with respect to the user's body part as indicated, at least in part, by the augmented classification. In a further detailed embodiment, the grooming implement is a dental appliance and the grooming implement is a motorized brush; and the step of modifying operation adjusts a speed setting of the motorized brush based upon the position of the grooming implement with respect to the user's mouth as indicated, at least in part, by the augmented classification. Alternatively, the grooming implement is a shaving appliance and the grooming implement is a motorized shaving head; and the step of modifying operation adjusts a speed setting of the shaving head based upon the position of the grooming implement with respect to the user's face as indicated, at least in part, by the augmented classification. Alternatively, the grooming implement is a shaving appliance and the grooming implement is a shaving cartridge; and the step of modifying operation adjusts an angle-of-attack setting of the shaving cartridge based upon the position of the grooming implement with respect to the user's face as indicated, at least in part, by the augmented classification. Alternatively, the step of modifying operation adjusts a pressure sensitivity setting of the grooming implement based upon the position of the grooming implement with respect to the user's body part as indicated, at least in part, by the augmented classification.

Alternatively, the augmented classification further includes a surface condition of the user's body part; and the step of modifying operation adjusts a performance setting of the grooming implement based upon a surface condition at the position of the grooming implement with respect to the user's face as indicated, at least in part, by the augmented classification. In a further detailed embodiment, the grooming appliance is a dental appliance and the surface condition pertains, at least in part, to presence of plaque on a user's teeth. Alternatively, the grooming appliance is a shaving appliance and the surface condition pertains, at least in part, to presence of whiskers on a user's face.

In another detailed embodiment of the first aspect, the augmented classification pertains, at least in part, to the position of the cleaning implement with respect to a household target surface, and the step of modifying operation modifies operation of the cleaning implement, based at least in part, upon the position of the of the cleaning implement with respect to the household target surface as indicated, at least in part, by the augmented classification.

In another detailed embodiment of the first aspect, the augmented classification detects an identity of the user of the grooming/household appliance and the modifying operation step applies an operation setting customized for the identified user.

It is a second aspect of the current disclosure to provide a system and method for operating a personal grooming appliance, including: providing a personal grooming/household appliance including at least one physical sensor taken from a group consisting of: an orientation sensor, an acceleration sensor, an inertial sensor, a global positioning sensor, a pressure sensor, and a load sensor, audio sensor, humidity sensor, and a temperature sensor; providing a camera associated with the personal grooming/household appliance; classifying data received from the physical sensor and from the camera using at least one trained machine learning classifier to generate an augmented classification; and providing user feedback information based upon the augmented classification; wherein the augmented classification pertains to a combination of a first state pertaining to a position of the grooming/household appliance with respect to a user's body-part or household target surface and also pertains to a second state that is different than the first state. In an embodiment, the second state pertains to an identity of a user. In an alternate embodiment, the second state pertains to an identity of the grooming appliance.

In an embodiment, the second state pertains to a surface condition of a user's body part. In a further detailed embodiment, the user's body part is a user's teeth and the surface condition pertains to the presence of plaque on the patient's teeth. Alternatively, the surface condition is the presence of whiskers or stubble on a user's body part. Alternatively, or in addition, the first state also pertains to a direction of movement of the personal grooming appliance. In a further detailed embodiment, the second state is an image classification derived from image data from the camera. In yet a further detailed embodiment, the image classification pertains to, at least in part, an identity of a shaving lubricant being used. Alternatively, or in addition, the second state is a stroke pressure classification derived from the physical sensor.

In an embodiment, the second state is an image classification derived from image data from the camera. In a further detailed embodiment, the image classification pertains to an emotion of a user of the grooming appliance. In yet a further detailed embodiment, the image classification pertains to a negative emotion of the user of the grooming appliance, and the feedback information provides advice for improving the user's experience with the grooming appliance.

In an embodiment, the image classification pertains to at least one of a pre-treatment or post-treatment condition. In a further detailed embodiment, the image classification pertains to a pre-treatment condition and the feedback information provides treatment instructions based upon the combination of pre-treatment condition and a position of the grooming/household appliance.

In an embodiment, the image classification pertains to an identity of an object used with grooming/household-cleaning along with the grooming/household appliance. In a further detailed embodiment, the feedback information includes marketing information (e.g., coupons, promotions, advertisements and the like) related to the object.

In an embodiment, the feedback information includes marketing information related to the image classification. In a detailed embodiment, the image classification pertains to a condition of a user's skin and the feedback information includes a recommended product for treating the skin condition. In a further detailed embodiment, the feedback information also includes a product application technique using the grooming appliance.

In an embodiment, the image classification pertains to a condition of a user's body part and the feedback information includes a recommendation for a product to apply to the body part along with a product application technique using the grooming appliance.

In an embodiment, the second state pertains to motion of the grooming/household appliance. Alternatively, or in addition, the step of generating the augmented classification is performed by a single classifier.

It is a third aspect of the current disclosure to provide a system and method for operating a personal grooming appliance, including: providing a personal grooming appliance including at least one motion sensor taken from a group consisting of: an orientation sensor, an acceleration sensor, and an inertial sensor; providing a camera associated with the personal grooming appliance; classifying data received from the motion sensor and from the camera using at least one trained machine learning classifier to generate an augmented classification; and providing user feedback information based upon the augmented classification; wherein the augmented classification pertains to a combination of a first state pertaining to a position of the grooming appliance with respect to a user's body part and also pertains to a second state that is different than the first classification. In a further detailed embodiment, the second state pertains to an identity of a user. Alternatively, the second state pertains to an identity of the grooming appliance. Alternatively, or in addition, the second state pertains to a surface condition of a user's body part. Alternatively, or in addition, the first state also pertains to a direction of movement of the personal grooming appliance.

In an embodiment the second state is an image classification derived from image data from the camera. In a further detailed embodiment, the image classification pertains to an emotion of a user of the grooming appliance. Alternatively, the image classification pertains to at least one of a pre-treatment or post-treatment condition. In a further detailed embodiment, the image classification pertains to a pre-treatment condition and the feedback information provides treatment instructions based upon the combination of pre-treatment condition and a position of the grooming appliance.

It is a fourth aspect of the current disclosure to provide a system and/or method for operating a personal grooming appliance, comprising: providing at least one of a camera associated with the personal grooming appliance or a bio-sensor associated with the personal grooming appliance; providing a personal grooming appliance having at least one motion sensor such as an orientation sensor, an acceleration sensor, and/or an inertial sensor; classifying at least one of image data received from the camera or bio-sensor data received from the bio-sensor to classify a surface condition of a surface of a user's anatomy using a first learning network classifier to generate an initial surface condition classification; generating user treatment information based upon the initial surface condition classification and communicating the user treatment information to the user; classifying motion data received from the motion sensor to classify motion of the personal grooming appliance with respect to the surface of the user's anatomy using a second learning network classifier to generate at least one of a relational motion classification or a relational position classification; generating user treatment progress information based upon a subsequent surface condition classification and based upon the at least one relational motion classification or relational position classification; and communicating the user treatment progress information to the user.

In an embodiment, the personal grooming appliance further includes a computer network interface transmitting and receiving data over a computer network; and the camera is located on a computerized device that includes a computer network interface at least transmitting image data over the computer network. In a further detailed embodiment, the method further includes a step of modifying operation of the grooming appliance based upon the user treatment progress information. Alternatively, or in addition, the step of generating user treatment information based upon the surface condition classification includes generating a treatment plan based, at least in part, on the surface condition information. In a further detailed embodiment, the treatment plan is implemented by a software application operating, at least in part, on the computerized device. In a further detailed embodiment, the treatment plan is customized for a user of the grooming appliance. Alternatively, or in addition, the user treatment progress information is reconciled against the treatment plan to determine treatment progress with respect to the treatment plan. Alternatively, or in addition, the method further includes a step of modifying the treatment plan based upon, at least in part, user treatment progress information. In an embodiment, the modifying step follows a step of determining that the initial surface condition classification is not correct. In an embodiment, the method further includes the step of communicating the modified treatment plan to the user.

It is a fifth aspect of the current disclosure to provide a system and/or method for operating a personal grooming appliance, including: providing a computerized device including a camera and a network interface that transmits image data from the camera over a computer network; providing a personal grooming appliance including, (a) an orientation sensor, an acceleration sensor, an inertial sensor, a pressure sensor, and/or a load sensor, and (b) a computer network interface transmitting and receiving data over the computer network; providing a software application operating, at least in part, on the computerized device; classifying image data received from the camera to generate an image classification using one or more learning network classifiers; generating a treatment plan based, at least in part, on the image classification; customizing the treatment plan based upon user information accessible to the software application; implementing at least a portion of the customized treatment plan by the software application; classifying sensor data received from the at least one sensor to classify use of the personal grooming appliance with respect to the surface of the user's anatomy, using one or more learning network classifiers, to generate a relational grooming appliance use classification; and generating user treatment plan progress information based upon the relational grooming appliance use classification and communicating the user treatment plan progress information to the user.

In a further detailed embodiment, the step of classifying image data includes identifying the user's anatomy. Alternatively, or in addition, the step of generating the relational grooming appliance use classification is based upon classifying a combination of the image data and the sensor data. Alternatively, or in addition, the method further includes a step of modifying operation of the grooming appliance based upon the relational grooming appliance use classification. Alternatively, or in addition, the user treatment progress information is reconciled against the treatment plan to determine treatment progress with respect to the treatment plan. Alternatively, or in addition, the user information accessible to the software application includes user profile information collected by the software application. Alternatively, or in addition, the user information accessible to the software application includes information derived from the relational grooming appliance use classification. Alternatively, or in addition, the method further includes the step of training the one or more learning network classifiers based upon how the user operates the grooming appliance. Alternatively, or in addition, the method further includes the step of training the one or more learning network classifiers based upon user information collected by the software application, where the user information may be collected by the software application is based, at least in part, upon the user's interactions with the software application.

It is a sixth aspect of the current disclosure to provide a method for treating a surface of a user's body part, including: obtaining target surface condition information from a user's body part surface using one or more condition sensors such an optical sensor and/or a bio-sensor; classifying the target surface condition information using a machine learning classifier to determine an initial target surface condition classification; obtaining treatment progress information using a combination of motion sensor data and surface condition information from the one or more condition sensors; and classifying the treatment progress information using a machine learning classifier to determine a progress classification for treating the initial target surface condition classification.

In a more detailed embodiment to the sixth aspect, the one or more condition sensors is provided on at least one of an examination instrument or a grooming appliance. Alternatively, or in addition, the method further includes displaying a representation of the treatment progress information. In an embodiment, he the displayed representation is a time-lapse representation; or, in another embodiment, the displayed representation is a real-time representation.

In a more detailed embodiment to the sixth aspect, the method includes modifying a setting of a treatment system based upon, at least in part, the treatment progress classification. In a further detailed embodiment, the modifying step occurs substantially in real time while the treatment system is treating the user's body part surface. In a further detailed embodiment, the one or more condition sensors is provided a treatment instrument of the treatment system. In yet a further detailed embodiment, the treatment instrument is an oral care instrument.

In a more detailed embodiment to the sixth aspect the method includes modifying settings of a treatment system based upon the target surface condition classification. Alternatively, or in addition, the method further includes evaluating change of the user's body part surface condition over time based upon successive target surface condition classifications. Alternatively, or in addition, the progress classification indicates that the initial target surface condition classification is incorrect. In such a case, the method may further include, generating an initial treatment plan based upon the initial treatment classification and modifying the initial treatment plan upon determining that the initial target surface condition classification is incorrect.

These and other aspects and objects of the current disclosure will become apparent by the following description, the appended claims and the attached drawings.

BRIEF DESCRIPTION OF THE DRAWINGS

In the following, embodiments of the present disclosure are described in more detail with reference to the figures, in which FIG. 8 shows a block diagram of a method according to an embodiment of the current disclosure, FIG. 12 shows a block diagram of a method according to an embodiment of the current disclosure, FIG. 13 a block diagram representation of a networked system according to embodiments of the current disclosure.

DETAILED DESCRIPTION

Figure 1:
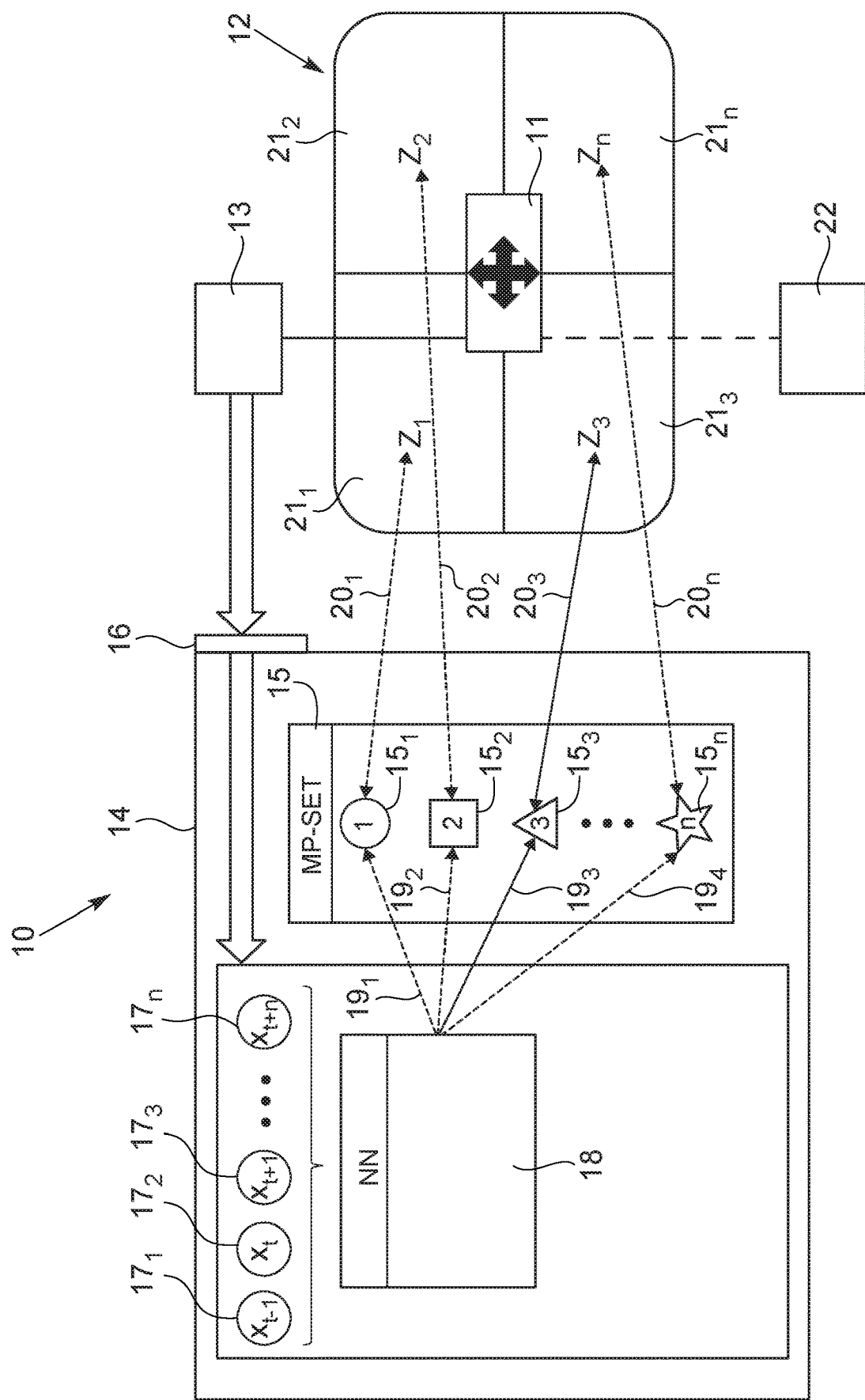
FIG. 1 shows a schematic block diagram of an apparatus according to an embodiment of the current disclosure.

Equal or equivalent elements or elements with equal or equivalent functionality may be denoted in the following description by equal or equivalent reference numerals. However, similar or equivalent elements may also be represented by different reference numerals based upon the embodiment.

In the following, reference will be made to personal grooming appliances and/or household appliances as non-limiting examples of "movable treatment devices." For example, personal grooming appliances, may include shaving appliances (manual shavers, electric shavers, trimmers, epilators, chemistry based hair removal and the like), dental appliances (manual toothbrushes, electric toothbrushes, polishers, waterjets, ultrasound appliances, flossing appliances and the like), scrubbers (exfoliating brushes and the like), cosmetic applicators, and hair styling appliances (hair brushes, trimmers/cutters, hair dryers, straighteners, curlers and the like). Such grooming appliances may also have certain medical and/or dental examination/diagnosis/treatment uses and will be described herein. In these examples, the surface to be treated is a portion of a user's anatomy, such a user's teeth, face, legs, etc. Also, household appliance may include surface cleaners, polishers, pressure-washers, floor cleaners, vacuum cleaners, window cleaners and the like. In these examples, the surface to be treated may be a household surface such as a floor, a wall, a counter-top, a sink, a window, a mirror, a vehicle surface, and the like.

Furthermore, an order of any method steps of a method may only be described as a non-limiting example. Accordingly, unless expressly stated as being performed in a specific order, any method steps as described herein may also be executed in any other order than described. Although some aspects will be described in the context of an apparatus or device, it will be understood that these aspects also represent a description of the corresponding method, where a block or device corresponds to a method step or a feature of a method step. Analogously, aspects described in the context of a method or method step also represent a description of a corresponding block or item or feature of a corresponding apparatus or device.

FIG. 1 shows an apparatus or system 10 according to an exemplary embodiment. A movable treatment device 11 is depicted. The movable treatment device 11 may comprise an inertial sensor 13. Furthermore, the movable treatment device 11 may be configured to treat a target surface 12. As will be described below, a camera 22 may also be associated with the device 11 (as will be described below a camera is "associated" in that the camera may be included as part of the treatment device 11 or the camera may be apart from the treatment device, such as in a handheld smartphone or in a smart display or mirror—essentially, any networked or wirelessly connected camera).

As can be seen, the movable treatment device 11 may be located at a certain position relative to a target surface 12, for example in, at, on or next to the target surface 12. The target surface 12 itself may be divided into one or more zones $21_1$, $21_2, 21_3, \ldots, 21_n$. The movable treatment device 11 may be moved or be located at a position relative to at least one of said zones $21_1, 21_2, 21_3, \ldots, 21_g$.

The apparatus 10, as depicted in FIG. 1, may be configured to perform a localization of the movable treatment device 11 relative to the target surface 12.

The apparatus 10 may comprise a motion pattern recognition device 14. The motion pattern recognition device 14 may be configured to discriminate between two or more movement classifications such as motion patterns $15_1, 15_2, 15_3, \ldots 15_n$ that are contained in a set 15 of motion patterns of the movable treatment device 11. In other words, the movable treatment device 11 may be moved, e.g. by a user using said movable treatment device 11, in different linear and/or rotational directions. Accordingly, each motion of the movable treatment device 11 may represent a respective or individual motion pattern. The motion pattern recognition device 14 may comprise a set 15 of different motion patterns. The set 15 of motion patterns may comprise two or more of said aforementioned respective or individual motion patterns $15_1, 15_2, 15_3, \ldots, 15_n$. The motion pattern recognition device 14 may be configured to discriminate between these two or more motion patterns $15_1, 15_2, 15_3, \ldots, 15n$. That is, the motion pattern recognition device 14 may be configured to distinguish a first motion pattern $15_1$ from a second motion pattern $15_2$.

The movement of the movable treatment device 11 may be detected by at least one inertial sensor 13. The inertial sensor 13 is a sensor based on inertia and may comprise at least one of an accelerometer, a gyroscope and a magnetometer. The inertial sensor 13 may provide sensor data representing at least one of a linear velocity, an angular velocity, a linear acceleration, an angular acceleration and a g-force. The inertial sensor 13 may be part of an inertial measurement unit comprising one or more inertial sensors.

The apparatus 10 may comprise an interface 16 for receiving at least one inertial sensor data $17_1, 17_2, 17_3, \ldots 17_n$ from the inertial sensor 13 and for providing the at least one inertial sensor data $17_1, 17_2, 17_3, \ldots 17_n$ to the motion pattern recognition device 14. The at least one inertial sensor data $17_1, 17_2, 17_3, \ldots 17_n$ represents a movement of the movable treatment device 11. In other words, when the movable treatment device 11 moves, the inertial sensor 13 senses this motion and creates at least one inertial sensor data $17_1, 17_2, 17_3, \ldots 17_n$. Accordingly, the at least one inertial sensor data $17_1, 17_2, 17_3, \ldots 17_n$ represents the respective motion of the moved treatment device 11.

The motion pattern recognition device 14 may comprise a neural network 18. The neural network 18 may be a deep learning network. The neural network 18 may be configured to receive the at least one inertial sensor data $17_1, 17_2, 17_3, \ldots$, and to map the at least one inertial sensor data $17_1, 17_2, 17_3, \ldots, 17_n$ to at least one of the motion patterns $15_1, 15_2, 15_3, \ldots, 15n$ contained in the set 15 of motion patterns. This mapping is indicated in FIG. 1 by means of the dashed and solid arrows $19_1, 19_2, 19_3, 19_4$. The arrow $19_3$ that is drawn in solid lines may exemplarily indicate that the neural network 18 successfully mapped the at least one inertial sensor data $17_1, 17_2, 17_3, \ldots, 17_n$ to the third motion pattern $15_3$.

The different motion patterns $15_1, 15_2, 15_3, \ldots, 15n$ that are contained in the set 15 are exemplarily symbolized by different geometrical shapes (circle, rectangle, triangle, star) merely for illustration purposes. The motion patterns of the movable treatment device 11 are, of course, not limited to these specific geometrical shapes.

According to the inventive principle, the motion patterns $15_1, 15_2, 15_3, \ldots, 15n$ are each associated with one or more different zones $21_1, 21_2, 21_3, \ldots 21_n$ of the target surface 12. This is indicated by means of the dashed and solid arrows $20_1, 20_2, 20_3, \ldots, 20_n$. As can be seen, the first motion pattern $15_1$ may be associated with a first zone $21_1$ of the target surface 12, as is indicated by the dashed arrow $20_1$. The second motion pattern $15_2$ may be associated with a second zone $21_2$ of the target surface 12, as is indicated by the dashed arrow $20_2$. The third motion pattern $15_3$ may be associated with a third zone $21_3$ of the target surface 12, as is indicated by the arrow $20_3$ that is drawn in solid lines. The fourth motion pattern $15_4$ may be associated with a fourth zone $21_4$ of the target surface 12, as is indicated by the dashed arrow $20_4$.

The arrow $20_3$ that is drawn in solid lines may exemplarily indicate that the third motion pattern $15_3$, to which the at least one inertial sensor data $17_1, 17_2, 17_3, \ldots 17_n$ was successfully mapped by the neural network 18, is associated with the third zone $21_3$ of the target surface 12.

Accordingly, the mapping of the at least one inertial sensor data $17_1, 17_2, 17_3, \ldots 17_n$ with the at least one motion pattern $15_1, 15_2, 15_3, \ldots, 15n$ indicates an estimation of the location of the movable treatment device 11 with respect to the one or more zones $21_1, 21_2, 21_3, \ldots 21_n$ of the target surface 12. In the present example, the mapping of the at least one inertial sensor data $17_1, 17_2, 17_3, \ldots 17_n$ with the third motion pattern $15_3$ indicates an estimation of the location of the movable treatment device 11 with respect to the third zone $21_3$ of the target surface 12.

In other words, the neural network 18 successfully mapped the received at least one inertial sensor data $17_1, 17_2, 17_3, \ldots, 17_n$ to the third motion pattern $15_3$. Since, according to this example, the third motion pattern $15_3$ is associated with the third zone $21_3$, the apparatus 10 retrieves the information that the movable treatment device 11 is located at the third zone $21_3$, or that the movable treatment device 11 at least was located at the third zone $21_3$ at the time when the at least one inertial sensor data $17_1, 17_2, 17_3, \ldots, 17_n$ was created.

Thus, the apparatus 10 may be configured to localize the movable treatment device 11 relative to the target surface 12 simply by means of the executed motion, or motion pattern, of the movable treatment device 11.

According to an embodiment, the movable treatment device 11 may be a personal grooming appliance and the target surface 12 may be a body portion to be treated by the movable treatment device 11.

For example, the movable treatment device 11 may be a razor or a groomer for shaving or grooming a body portion of a user's body. The user's body (or a part of the body) may be the target surface 12 in this case. The user's body 12 may be separated into different zones, for instance, a left cheek zone, a right cheek zone, a chin zone and so on. By executing a predetermined motion pattern with the razor 11 the apparatus 10 may localize the razor 11 relative to the user's body. For instance, if the razor 11 executes a motion pattern that is directed into an upper left corner with the razor 11 being tilted to the left, the apparatus 10 may localize the razor 11 as being located in the left cheek zone, for example. Accordingly, the apparatus 10 may localize the razor 11 at the user's face simply by its executed motion pattern.

As a further example, the movable treatment device 11 may be a household appliance and the target surface 12 may be a surface of a floor, a wall, a furniture or the like. For example, the movable treatment device 11 may be a vacuum cleaner and the target surface 12 may be the floor of a room. The room 12 may be separated into different zones, for instance, a left top corner of the room, a right bottom corner of the room, a center of the room, underneath a bed located inside the room, and so on. By executing a predetermined motion pattern with the vacuum cleaner 11 the apparatus 10 may localize the vacuum cleaner 11 relative to the floor of the room. For instance, if the vacuum cleaner 11 executes a motion pattern that is merely directed forwards and backwards with the lance of the vacuum cleaner 11 being lowered near to the ground, the apparatus 10 may localize the vacuum cleaner 11 as being located in the "underneath the bed" zone, for example. Accordingly, the apparatus 10 may localize the vacuum cleaner 11 inside the room simply by its executed motion pattern.

According to a further embodiment, the movable treatment device 11 may be an oral care device and the target surface 12 may be a dentition, wherein the dentition 12 is separated into different dental zones $21_1, 21_2, 21_3, \ldots, 21_n$, wherein the mapping of the at least one inertial sensor data $17_1, 17_2, 17_3, \ldots 17_n$ with the at least one motion pattern $15_1, 15_2, 15_3, \ldots, 15n$ indicates an estimation of the location of the oral care device 11 with respect to the one or more dental zones $21_1, 21_2, 21_3, \ldots, 21_n$ of the dentition 12.

The oral care device may be a toothbrush, in particular an electric toothbrush. The oral care device may also be at least one of a dental floss, a polisher, a plaque removing device, an ultrasound device and a waterjet device. In some embodiments, the oral care device may also be an oral examination device.

According to this example, by executing a predetermined motion pattern with the oral care device 11 the apparatus 10 may localize the oral care device 11 relative to the dentition. For instance, if the oral care device 11 executes a motion pattern that is merely directed upwards and downwards with the oral care device 11 being tilted to the left, the apparatus 10 may localize the oral care device 11 as being located in a left upper dental zone of the upper jaw, for example. Accordingly, the apparatus 10 may localize the oral care device 11 relative to the user's dentition simply by its executed motion pattern.

According to an embodiment, the dentition may be separated into nine dental zones, wherein a first dental zone corresponds to the left buccal side of the upper and lower jaw of the dentition, a second dental zone corresponds to the occlusal side of the left and right side of the upper jaw of the dentition, a third zone corresponds to the occlusal side of the left and right side of the lower jaw of the dentition, a fourth dental zone corresponds to the left lingual side of the upper and lower jaw of the dentition, a fifth dental zone corresponds to the right buccal side of the upper and lower jaw of the dentition, a sixth dental zone corresponds to the right lingual side of the upper and lower jaw of the dentition, a seventh dental zone corresponds to the labial side of the upper and lower jaw of the dentition, an eighth dental zone corresponds to the palatal side of the upper jaw of the dentition, a ninth dental zone corresponds to the oral side of the front lower jaw of the dentition.

According to a further embodiment, at least one predetermined motion pattern 15NB that may be additionally contained in the set 15 of motion patterns may be associated with a zone 21NB outside the target surface 12, or not related to the target surface 12, wherein the mapping of the at least one inertial sensor data $17_1, 17_2, 17_3, \ldots 17_n$ with the at least one predetermined motion pattern 15NB indicates that the movable treatment device 11 is located in said zone 21NB that is outside the target surface 12, or not related to the target surface 12.

In other words, the zone 21NB outside the target surface 12 may be a zone that is not directly related to the target surface 12. For example, if the movable treatment device 11 may be a toothbrush, then said zone 21NB outside the target surface 12 may be a zone outside the dentition. Accordingly, this zone 21NB may indicate that the user is not brushing his teeth. Thus, this zone may also be referred to as a zone 'Not Brushing', abbreviated by 'NB'. This zone 21NB may be the at least one zone of the target surface 12, or this zone 21NB may be an additional zone in addition to the one or more zones $21_1, 21_2, 21_3, \ldots, 21_n$ of the target surface. However, this particular zone 21NB outside the target surface 12 is not limited to the above described example of teeth brushing.

Figure 2:
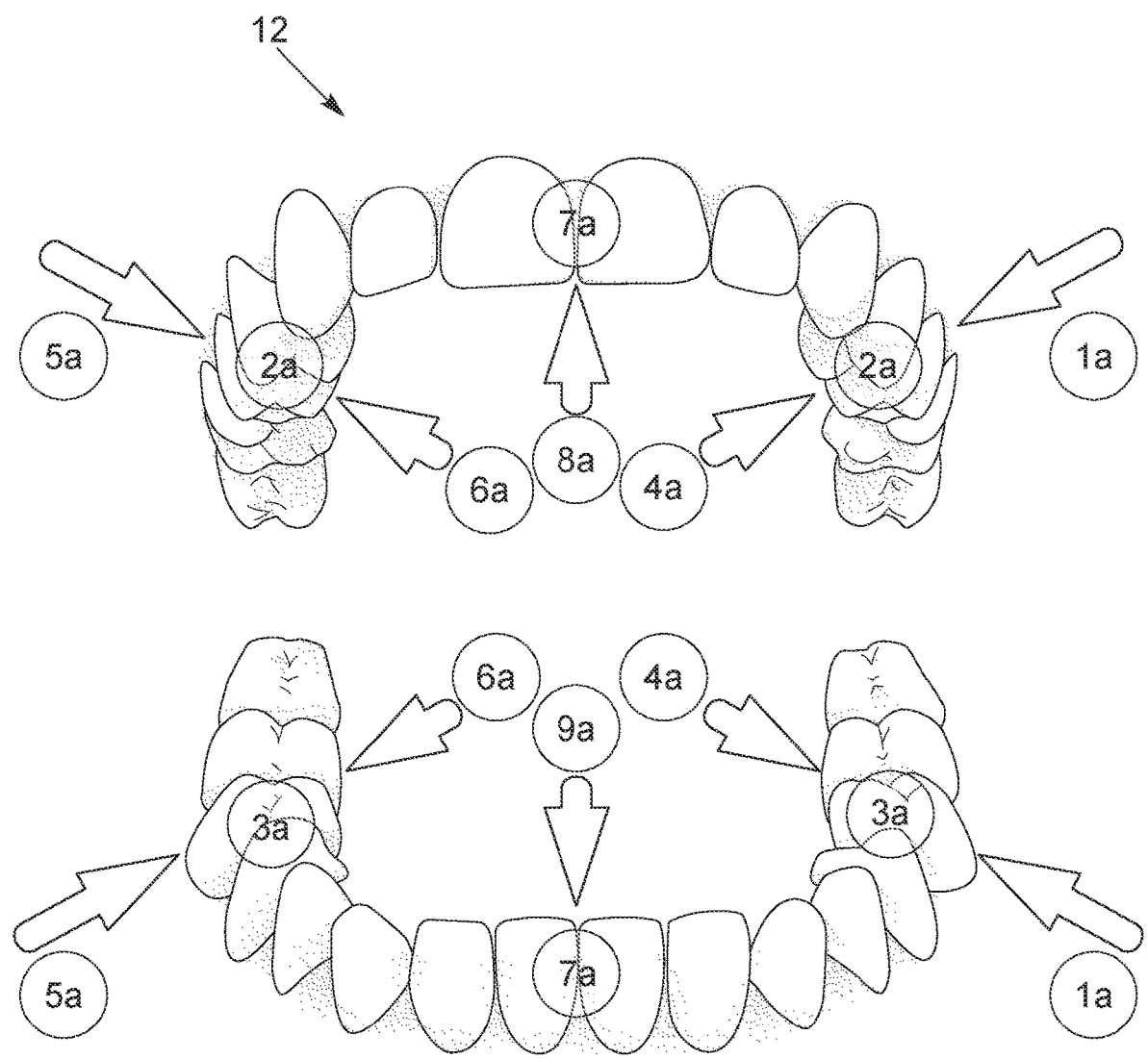
FIG. 2 shows an example of a target surface to be treated with the movable treatment device.

FIG. 2 shows a dentition 12 for illustrating the above described example. The dentition 12 may be the target surface. The dentition 12 may be separated into nine dental zones 1a to 9a. Optionally, a tenth zone NB may exist. This tenth zone NB is a zone outside the dentition 12. Thus, this tenth zone NB is not explicitly illustrated in FIG. 2. Since this tenth zone NB is not related to one of the dental zones of the dentition 12, and therefore not concerned with brushing the teeth of the dentition 12, this tenth zone NB may also be referred to as a 'Not Brushing' zone. As can be seen in FIG. 2, a first dental zone 1a may correspond to the left buccal side of the upper and lower jaw of the dentition 12. A second dental zone 2a may correspond to the occlusal side of the left and right side of the upper jaw of the dentition 12. A third zone 3a may correspond to the occlusal side of the left and right side of the lower jaw of the dentition 12. A fourth dental zone 4a may correspond to the left lingual side of the upper and lower jaw of the dentition 12. A fifth dental zone 5a may correspond to the right buccal side of the upper and lower jaw of the dentition 12. A sixth dental zone 6a may correspond to the right lingual side of the upper and lower jaw of the dentition 12. A seventh dental zone 7a may correspond to the labial side of the upper and lower jaw of the dentition 12. An eighth dental zone 8a may correspond to the palatal side of the upper jaw of the dentition 12. A ninth dental zone 9a may correspond to the oral side of the front lower jaw of the dentition 12.

Figure 3:
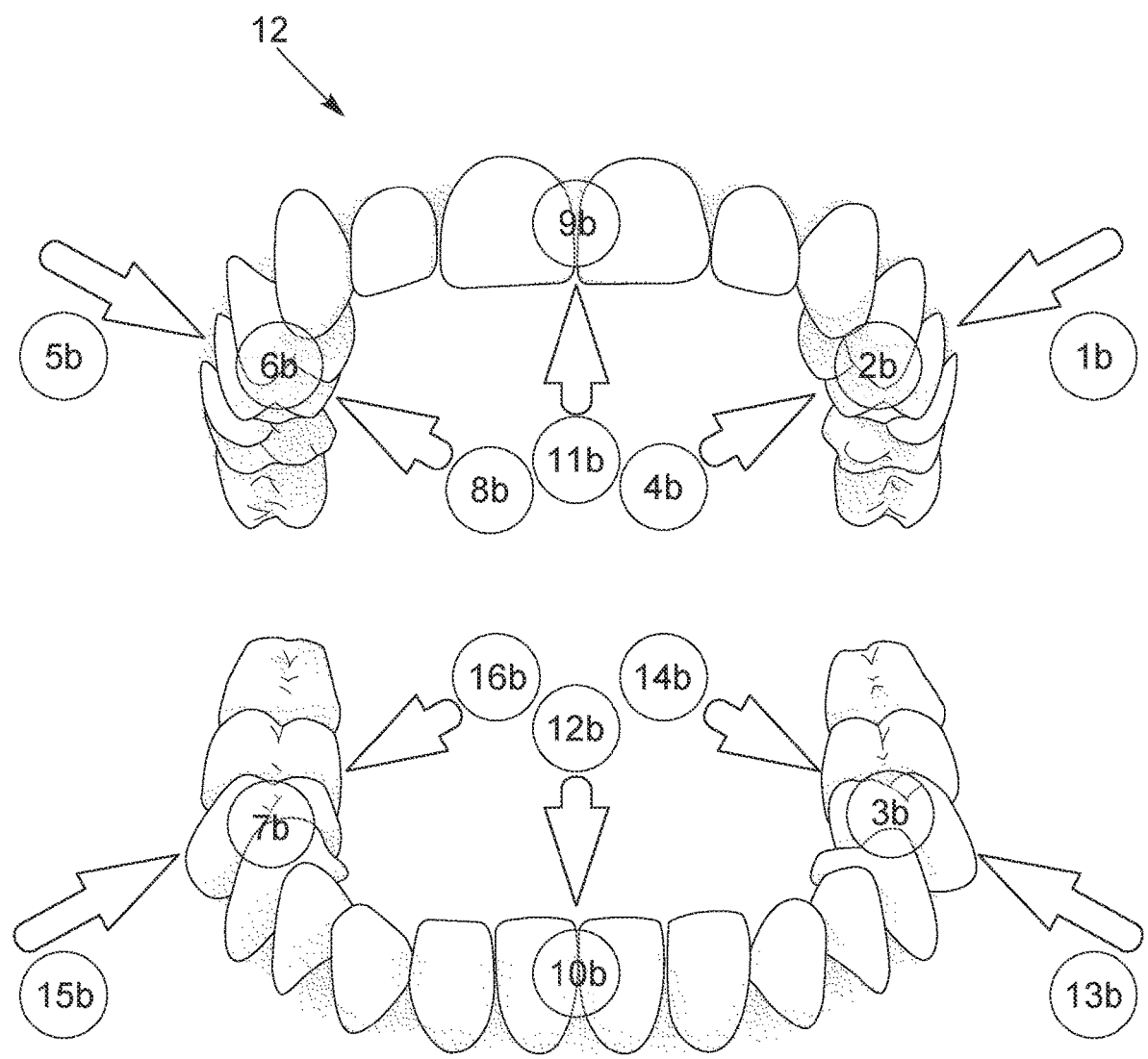
FIG. 3 shows a further example of a target surface to be treated with the movable treatment device.

FIG. 3 shows a dentition 12 for illustrating a further example. The dentition 12 may be the target surface. The dentition 12 may be separated into sixteen dental zones 1b to 16b. Optionally, a seventeenth zone NB may exist. This seventeenth zone NB is a zone outside the dentition 12. Thus, this seventeenth zone NB is not explicitly illustrated in FIG. 3. Since this seventeenth zone NB is not related to one of the dental zones of the dentition 12, and therefore not concerned with brushing the teeth of the dentition 12, this seventeenth zone NB may also be referred to as a 'Not Brushing' zone.

As can be seen in FIG. 3, a first dental zone 1b may correspond to the left buccal side of the upper jaw of the dentition 12. A second dental zone 2b may correspond to the occlusal side of the left side of the upper jaw of the dentition 12. A third dental zone 3b may correspond to the occlusal side of the left side of the lower jaw of the dentition 12. A fourth dental zone 4b may correspond to the left lingual side of the upper and lower jaw of the dentition 12. A fifth dental zone 5b may correspond to the right buccal side of the upper and lower jaw of the dentition 12. A sixth dental zone 6b may correspond to the occlusal side of the right side of the upper jaw of the dentition 12. A seventh dental zone 7b may correspond to the occlusal side of the right side of the lower jaw of the dentition 12. An eighth dental zone 8b may correspond to the palatal side of the upper jaw of the dentition 12. A ninth dental zone 9b may correspond to labial side of the upper jaw of the dentition 12. A tenth dental zone 10b may correspond to the labial side of the lower jaw of the dentition 12. An eleventh dental zone 11b may correspond to the palatal side of the upper jaw of the dentition 12. A twelfth dental zone 12b may correspond to the oral side of the front lower jaw of the dentition 12. A thirteenth dental zone 13b may correspond to the left buccal side of the lower jaw of the dentition 12. A fourteenth dental zone 14b may correspond to the left lingual side of the lower jaw of the dentition 12. A fifteenth dental zone 15b may correspond to the right buccal side of the lower jaw of the dentition 12. A sixteenth dental zone 16b may correspond to the right lingual side of the lower jaw of the dentition 12.

FIGS. 2 and 3 have only been described as non-limiting examples. The target surface 12 may also comprise more or less than the exemplarily described nine or sixteen dental zones. Furthermore, the tenth/seventeenth dental zone NB outside the target surface 12 is optional. The exact distribution of the one or more dental zones of the dentition 12 may vary from the examples described above.

The apparatus 10 may be self-learning as regards the localization of the movable treatment device relative to the target surface 12. The apparatus 10 may make use of artificial intelligence, for instance, by exploiting deep learning networks. For example, the apparatus 10 may make use of classifiers developed by artificial intelligence and/or learning networks; and further, the apparatus 10 (and the systems described herein) may further teach such classifiers. Accordingly, the apparatus 10 for performing the localization of the movable treatment device 11 relative to the target surface 12 may enhance its performance over time by using the neural network 18.

According to an embodiment, the neural network 18 may be a Recurrent Neural Network (RNN).

For example, the neural network may be a Long Short Term Memory (LSTM) network or a Gated Recurrent Unit (GRU) network.

RNNs may suffer from the so-called vanishing gradient problem, wherein gradients vanish quickly with more number of layers. Vanishing gradients may lead to rather slow training rates. Thus, LSTM networks and/or GRU networks may be used to avoid the vanishing gradient problem.

An LSTM network is an artificial neural network containing LSTM blocks in addition to regular network units. An LSTM block contains gates that determine when the input is significant enough to remember, when it should continue to remember or when it should forget the value, and when it should output the value.

Figure 4:
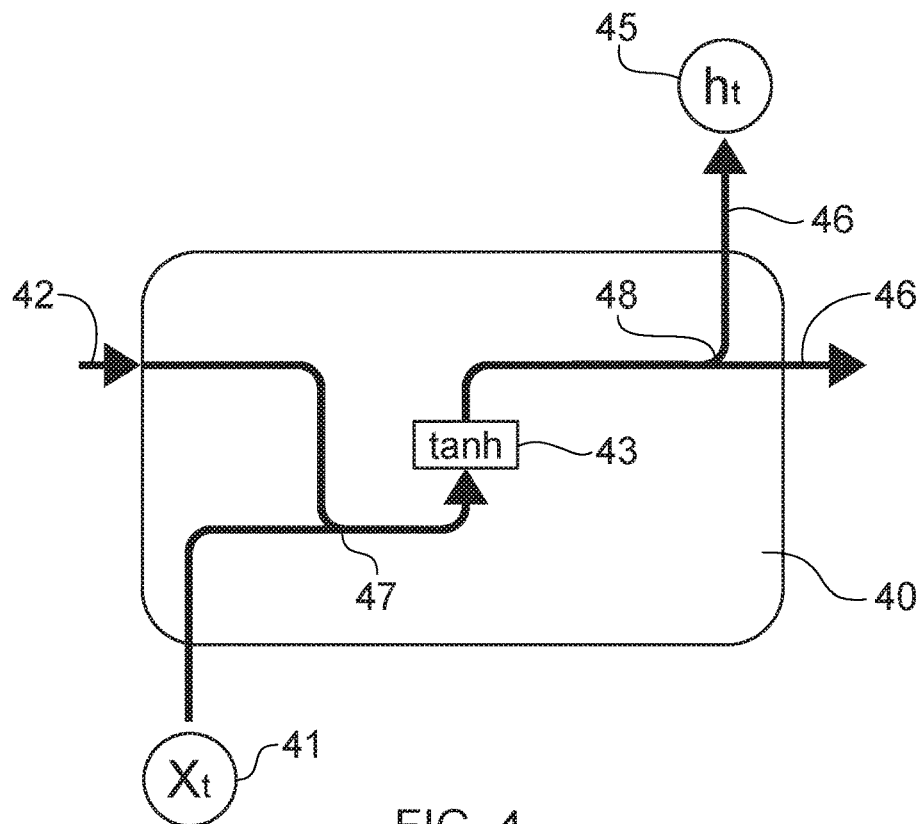
FIG. 4 shows a schematic block diagram of a recurrent neural network that may be used in embodiments disclosed herein.

FIG. 4 shows an example for a RNN in its most general form. A neural unit 40 may be fed with an input 41 at a certain time instant t. The input 41 may be a single value or a vector comprising two or more values. The input 41 at the certain time instant t may also be symbolized with Xt.

The neural unit 40 may optionally also comprise a further input 42. This further input 42 may be provided from a neural unit (not depicted here) at a previous time instant t−1.

The neural unit 40 may comprise at least one gate 43, which may provide a mathematical operation. In this example, the gate 43 is a single tan h gate.

The neural unit 40 may comprise at least one output 46. The output 46 may comprise the result of the operation of the tan h gate 43 that has been fed with the input 41 and optionally the further input 42. The output 46 may lead to a hidden state 45, which will be explained later.

The neural unit 40 may optionally comprise a further output branch 46 which branches off from the above mentioned output result of the operation of the tan h gate 43 fed with the input 41 and optionally the further input 42.

In FIG. 4, each depicted line may carry an entire vector, from the output of one node to the inputs of others. Lines merging, for instance at 47, denote concatenation, while a line forking, for instance at 48, denote its content being copied and the copies going to different locations. This holds true also for the other neural networks that will be described in the following with reference to the following Figures.

Figure 5:
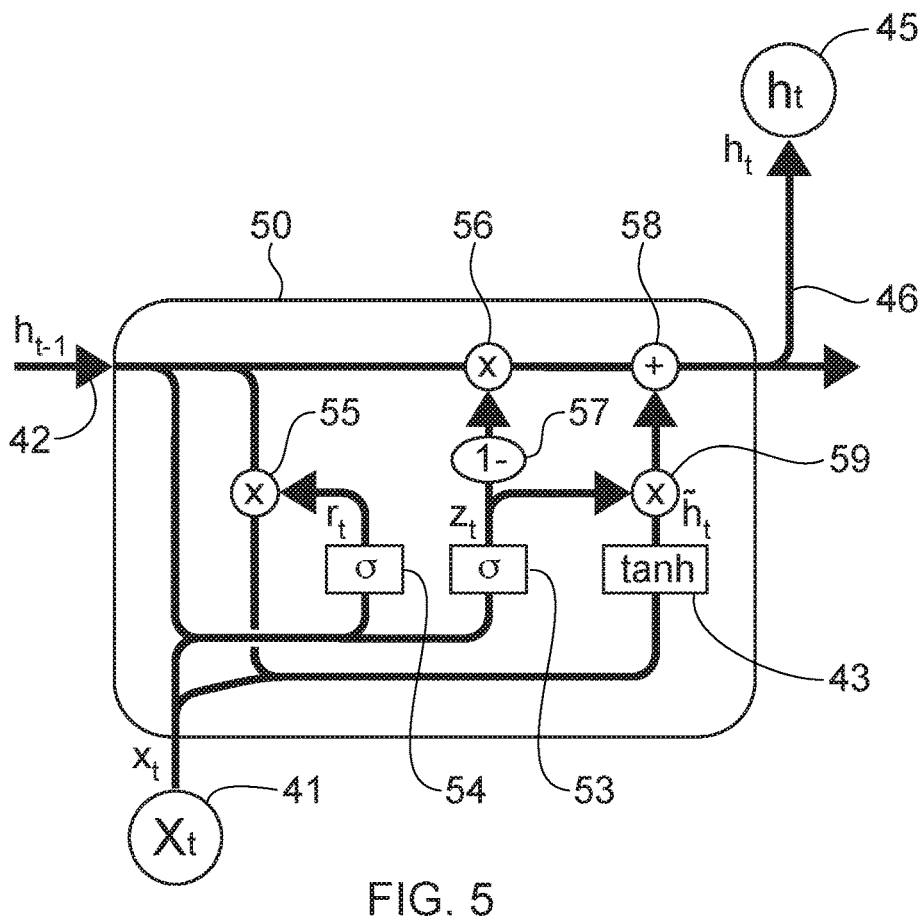
FIG. 5 shows a schematic block diagram of a GRU neural network that may be used in embodiments disclosed herein.

FIG. 5 shows an example of a GRU network. The GRU network comprises a neural unit 50. In addition to the above described RNN neural unit 40, the GRU neural unit 50 may comprise two further gates, namely a first sigmoid gate 53 and a second sigmoid gate 54. Furthermore, the GRU neural unit 50 may comprise pointwise operations 55, 56, 57, 58, 59, like vector addition 58, for example.

Figure 6A:
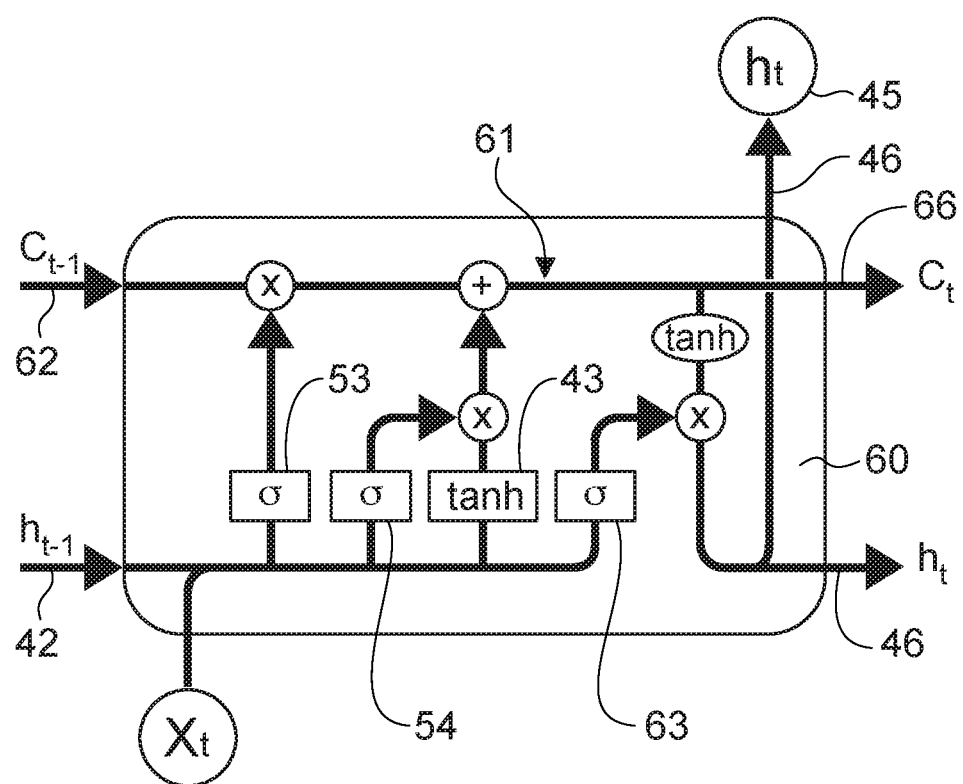
FIG. 6A shows a schematic block diagram of an LSTM neural network that may be used in embodiments disclosed herein.

FIG. 6A shows an example of an LSTM network that may be exploited as the neural network 18 in the apparatus 10. The LSTM may comprise a neural unit 60 which may, in the case of LSTM networks, also be referred to as an LSTM block. In addition to the above described neural units 40, 50, the neural unit 60 of the depicted LSTM network may comprise a cell state, which is the horizontal line 61 running through the top of the neural unit 60. The neural unit 60 may receive a cell state input 62 and may create a cell state output 66.

The neural unit 60 may further comprise four gates 43, 53, 54, 63. For example, it may comprise a further sigmoid gate 63 compared to the GRU network described above. Information may be removed or added to the cell state (horizontal line 61) by means of these gates 43, 53, 54, 63.

Figure 6B:
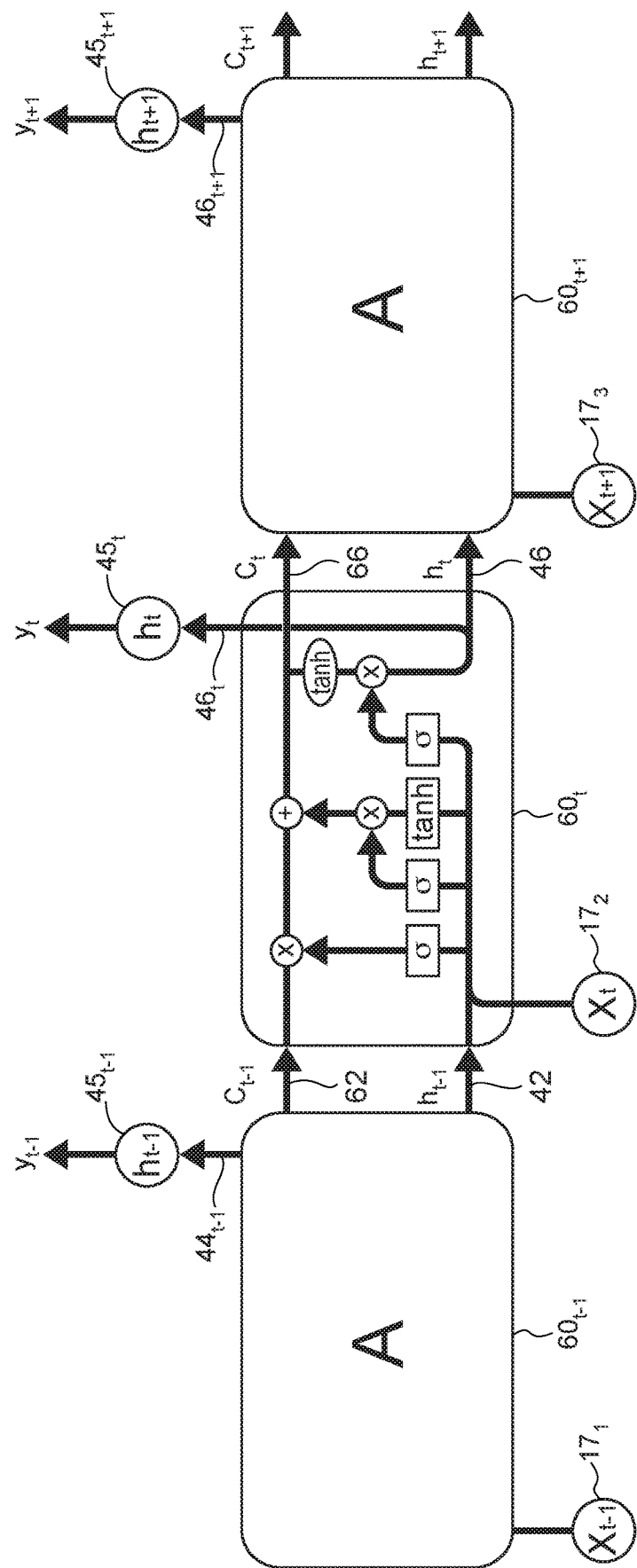
FIG. 6B shows a schematic block diagram of an LSTM neural network with one layer at different time instances.

FIG. 6B shows a further example in which previous and subsequent states (with respect to the time instant t) of the neural unit are depicted. In particular, a neural unit 60t at a time instant t is depicted. Furthermore, a further neural unit 60t−1 at a previous time instant t−1 is depicted. Still further a further neural unit 60t+1 at a subsequent time instant t+1 is depicted. The depicted neural units 60t−1, 60t, 60t+1 may represent the same neural unit but at different points in time, namely at the time instant t, at a previous time instant t−1 and at a subsequent time instant t+1. The above described input 41, also symbolized by the letter X, may comprise the at least one sensor data $17_1$, $17_2$, $17_3$, . . . $17_n$ from the inertial sensor 13. The input X may be time dependent, thus X=X(t). In particular, the depicted input Xt may comprise a sensor data $17_2$ acquired during the considered time instant t, the depicted input Xt−1 may comprise a sensor data $17_1$ acquired during a previous time instant t−1, and the depicted input Xt+1 may comprise a sensor data $17_3$ acquired during a subsequent time instant t+1.

As can further be seen in FIG. 6B, the neural unit 60t−1, 60t, 60t+1 may, in each depicted time instant t−1, t, t+1, provide, for instance by prediction, a respective output value yt−1, yt, yt+1. The output value y(t) may be a single value or a vector comprising one or more vector elements.

The output value y(t) may be calculated as:

$$yt = \text{softmax}(Why \cdot ht + b)$$

The output value y(t) may, for instance, comprise probabilistic values, as will be explained in more detail with respect to FIG. 7. For example, the output value y(t) may be a vector comprising one or more vector elements, wherein each vector element may represent one of the motion patterns $15_1$, $15_2$, $15_3$, . . . , $15n$, or in more detail wherein each vector element may represent a probabilistic value indicating how probable it is that the input X(t), i.e. the inertial sensor data $17_1$, $17_2$, $17_3$, . . . , $17n$, may correspond to one of the motion patterns $15_1$, $15_2$, $15_3$, . . . , $15_n$.

Furthermore, the depicted neural units 60t−1, 60t, 60t+1 may be arranged in the same layer, namely in a first layer. Some examples may comprise one or more further layers, wherein each layer may comprise its own neural unit(s). Such examples may be described later with reference to FIG. 7 for example. However, examples and embodiments with at least a first layer will be described with further reference to FIG. 6B.

According to this embodiment, the neural network 18 may comprise a first layer, wherein said first layer comprises a neural unit 60t, wherein at a first time instant t the at least one inertial sensor data Xt $17_2$ is input into the neural unit 60t of the first layer. At a subsequent second time instant t+1 a second inertial sensor data Xt+1 173 and at least one output ht 46 of the neural unit 60t of the previous first time instant t are input into the neural unit 60t+1 of the first layer.

Figure 7:
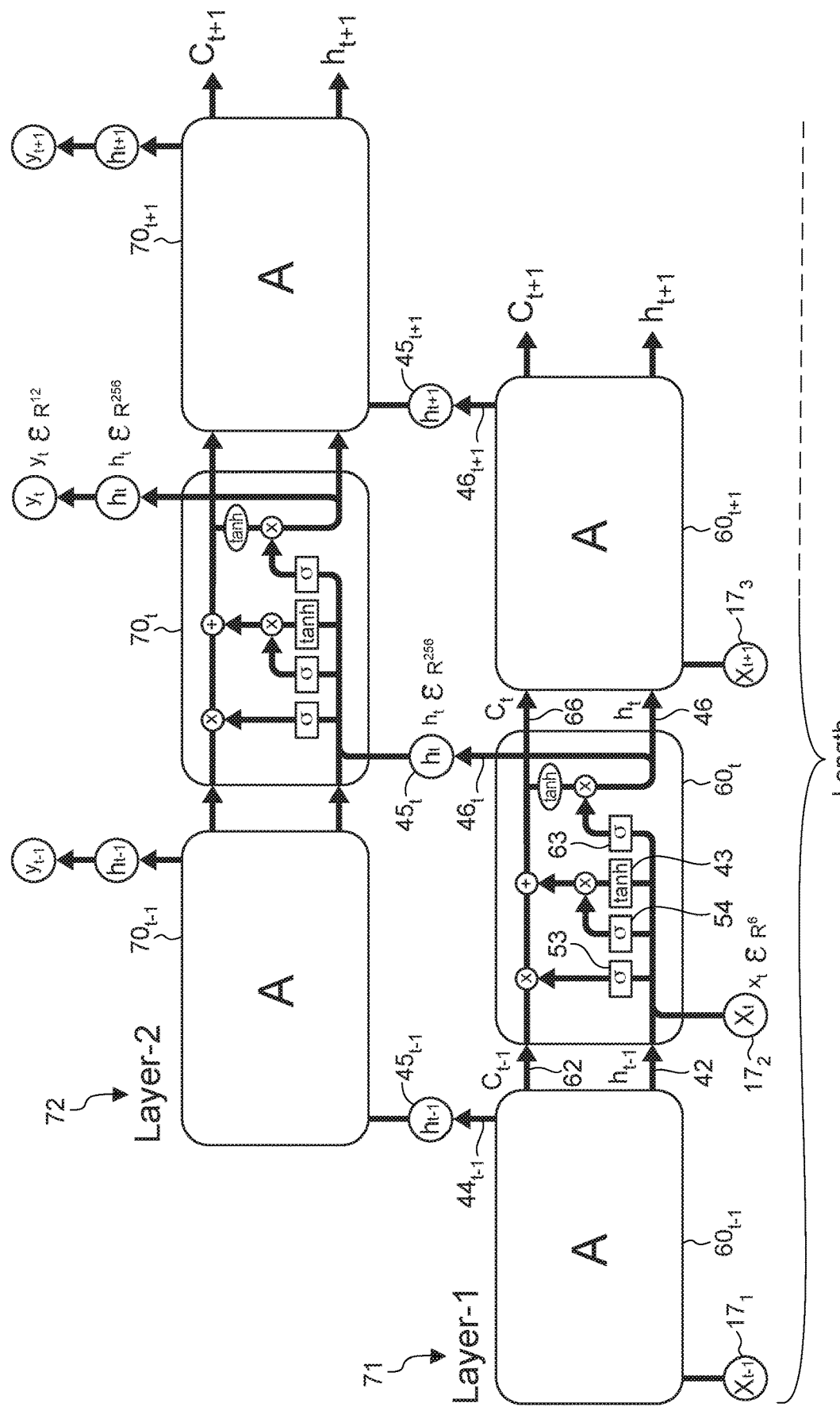
FIG. 7 shows a schematic block diagram of an LSTM neural network with two layers at different time instances.

FIG. 7 shows a further example, wherein the neural network 18 may comprise at least two layers, namely a first layer 71 and a second layer 72. The first layer 71 comprises at least a first neural unit 60t, and the second layer 72 comprises at least a second neural unit 70t.

As can be seen, the sensor data $17_1$, $17_2$, $17_3$ that is acquired during different time instances t−1, t, t+1 may be fed as input Xt−1, Xt, Xt+1 into the respective neural unit 60t−1, 60t, 60t+1 of the first layer 71.

The output 46t−1, 46t, 46t+1 of each neural unit 60t−1, 60t, 60t+1 of the first layer 71 may be fed as an input into the respective neural units 70t−1, 70t, 70t+1 of the second layer 72.

The neural units 60t−1, 60t, 60t+1 of the first layer 71 and the neural units 70t−1, 70t, 70t+1 of the second layer 72 may be identical. Alternatively, the internal structure of the neural units 60t−1, 60t, 60t+1 of the first layer 71 and the neural units 70t−1, 70t, 70t+1 of the second layer 72 may differ from each other.

According to the embodiment as shown in FIG. 7, the neural network 18 may comprise at least a first layer 71 and a second layer 72, wherein the first layer 71 may comprise a first neural unit 60t and wherein the second layer 72 may comprise a second neural unit 70t, wherein at a first time instant t the at least one inertial sensor data Xt $17_2$ is input into the first neural unit 60t of the first layer 71, and wherein an output ht 46 of the first neural unit 60t is input into the neural unit 70t of the second layer 72.

So far a signal path in a vertical direction, i.e. from a bottom first layer 71 to a top second layer 72 has been described. However, in the embodiment of FIG. 7 also a signal path in a horizontal direction is shown.

As can be seen, the cell state output Ct 66 of a first neural unit 60t at a first time instant t and/or the output ht 46 of the first neural unit 60t at the first time instant t may be fed as an input into the first neural unit 60 again, namely into the first neural unit 60t+1 at a subsequent time instant t+1. As already mentioned above, the neural unit 60 itself may be the same neural unit but it may only be depicted in the Figures as a plurality of concatenated neural units 60t−1, 60t, 60t+1 for ease of illustration of the states of the neural unit 60 at the different time instances t−1, t, t+1. In other words, the horizontal signal path may describe the signal path of the neural unit 60 at different subsequent time instances t−1, t, t+1. The same holds true for the second layer 72 and any further layers.

Accordingly, the depicted subsequent time instances t−1, t, t+1 may represent a length 77 during which the neural network 18 may sample and process the acquired sensor data $17_1$, $17_2$, $17_3$, . . . , $17_n$. Said length 77 may therefore be referred to as a run length, a sample length or a sample period. For example, the sample length 77 may correspond to one second, wherein the time instances t−1, 5 t, t+1 may be fractions of said one second. For example a sample period 77 may have a length of fifty samples, i.e. of fifty time instances. The neural network 18 may run once during a sample period, or the neural network 18 may run permanently over two or more sample periods.

Thus, according to a further embodiment, the neural network 18 may comprise at least a first layer 71 and a second layer 72, wherein the first layer 71 may comprise a first neural unit 60t and wherein the second layer 72 may comprise a second neural unit 70t, wherein at a first time instant t the at least one inertial sensor data Xt $17_2$ may be input into the first neural unit 60t of the first layer 71, and wherein at least one output ht 46 of the first neural unit 60t may be input into the neural unit 70t of the second layer 72. So far it may be the same as described above. However, additionally, at a subsequent second time instant t+1, a second inertial sensor data Xt+1 $17_3$ and at least one output ht 46 of the first neural unit 60t at the first time instant t is input into the first neural unit 60t+1 at the subsequent second time instant t+1.

As mentioned above, several mathematical operations may be executed by the neural network 18, in the gates 43, 53, 54, 63. In the example shown in FIG. 7 the following mathematical operations may be executed at the different stages:

$$\begin{vmatrix} \tilde{h}_j = \sum_{k \in C(j)} h_k, \\ i_j = \sigma(W^{(i)}x_j + U^{(i)}\tilde{h}_j + b^{(i)}), \\ f_{jk} = \sigma(W^{(f)}x_j + U^{(f)}h_k + b^{(f)}), \\ o_j = \sigma(W^{(o)}x_j + U^{(o)}\tilde{h}_j + b^{(o)}), \\ u_j = \tanh(W^{(u)}x_j + U^{(u)}\tilde{h}_j + b^{(u)}), \\ c_j = i_j \odot u_j + \sum_{k \in C(j)} f_{jk} \odot c_k, \\ h_j = o_j \odot \tanh(c_j), \end{vmatrix}$$

wherein
i(t) is the input gate's activation vector
f(t) is the forget gate's activation vector
o(t) is the output gate's activation vector
c(t) is the cell state vector
h(t) is the output vector of an LSTM block or neural unit 60, 70

According to this example, the input sensor data Xt 172 may be an element vector Xt∈$\mathbb{R}^6$. For example it may be an input tensor Xt∈$\mathbb{R}^6$, $[Ax, Ay, Az, Gx, Gy, Gz]^T$ Furthermore weights W(t) and bias values b(t) are depicted in FIG. 7, wherein in this example:
Weights Why∈$\mathbb{R}^{12 \times 256}$
Bias bt∈$\mathbb{R}^{12}$ Furthermore, the output vector y(t) may be calculated as:

$$yt = \text{softmax}(Why \cdot ht + b)$$

The depicted hidden states h(t) may also be element vectors, for example element vectors comprising 256 elements ht∈$\mathbb{R}^{256}$.

Furthermore, the depicted hidden states C(t) may also be element vectors, for example element vectors comprising 256 elements Ct∈$\mathbb{R}^{256}$.

As mentioned above, the input inertial sensor data Xt $17_2$ may be an element vector Xt∈$\mathbb{R}^6$ comprising six vector elements, for example an input tensor Xt∈$\mathbb{R}^6$, $[Ax, Ay, Az, Gx, Gy, Gz]^T$. These vector elements [Ax, Ay, Az, Gx, Gy, Gz]$^T$ may also be referred to as inertial sensor data portions.

According to an embodiment, the at least one inertial sensor data $17_1$ may comprise at least three inertial sensor data portions of the group comprising a linear velocity in x, y and z direction, an angular velocity with respect to the x, y and z axes, a linear acceleration in x, y and z direction, and an angular acceleration with respect to the x, y and z axes.

In other words, the inertial sensor 13 may provide inertial sensor data $17_1$, $17_2$, $17_3$, . . . , $17_n$ at the one or more time instances t−1, t, t+1, wherein the inertial sensor data $17_1$, $17_2$, $17_3$, . . . , $17_n$ may depend on the current orientation and motion of the movable treatment device 11 at one observed time instance t−1, t, t+1. Each of the inertial sensor data $17_1$, $17_2$, $17_3$, . . . $17_n$ may be a vector comprising at least three, or in other examples at least six vector elements, wherein said vector elements represent the above mentioned inertial sensor data portions, wherein at least one of said inertial sensor data portions may be zero.

Accordingly, the inertial sensor data $17_1$, $17_2$, $17_3$, . . . $17_n$(vectors), and in particular the sensor data portions (vector elements), may represent the current motion pattern of the movable treatment device 11 as sampled during a sample period 77 comprising one or more subsequent time instances t−1, t, t+1.

According to an embodiment as depicted in FIG. 7, the at least one inertial sensor data $17_2$ (vector) may comprise one or more inertial sensor data portions (vector elements), wherein an input to the neural unit $60t$ at a first time instant t is a respective inertial sensor data $17_2$ comprising the one or more inertial sensor data portions retrieved during said first time instant t. At least one inertial sensor data $17_1$, $17_2$, $17_3$, ... $17_n$ may be sampled during a sample time 77.

The neural network 18 may map the at least one sampled inertial sensor data $17_1$, $17_2$, $17_3$, ... $17_n$ which has been sampled during the sample time 77 to at least one motion pattern $15_1$, $15_2$, $15_3$, ..., $15_n$ contained in the set 15 of motion patterns, as it was initially described with reference to FIG. 1. After mapping, the selected one motion pattern may be referred to as a mapped motion pattern.

In other words, the neural network 18 may receive the inertial sensor data $17_1$, $17_2$, $17_3$, ..., $17_n$ as an input x(t) and it may output one or more probability values as an output y(t). As mentioned above, in the example shown in FIG. 7, the output value y(t) may also be an element vector comprising for example at least three, or at least six, or at least twelve vector elements. Each vector element of the output vector y(t) may represent a probabilistic value for a motion pattern $15_1$, $15_2$, $15_3$, ..., $15_n$ that may be associated with a class or a zone $21_1$, $21_2$, $21_3$, ..., $21_n$. In some embodiments, the output value y(t) may be an element vector comprising, for example, at least two to as many needed classes or zones, for example nine zones, twelve zones or sixteen zones.

Accordingly, the output vector y(t) may represent the different zones $21_1$, $21_2$, $21_3$, ... $21_n$ of the target surface 12. For example, if the target surface 12 may comprise twelve zones (e.g. eleven dental zones and a twelfth zone 'NB' for not brushing) then the element output vector y(t) may comprise twelve vector elements, such as shown in the example of FIG. 7, wherein $y(t) \in \mathbb{R}^{12}$. Accordingly, each vector element may represent one of the different zones $21_1$, $21_2$, $21_3$, ..., $21_n$ of the target surface 12.

As mentioned before, the vector elements may represent probability values. These probability values may represent the probabilistic value for each of the different zones $21_1$, $21_2$, $21_3$, ..., $21_n$ of the target surface 12. In other words, the neural network 18 may receive the at least one inertial sensor data $17_1$, $17_2$, $17_3$, ..., $17_n$ and map the at least one inertial sensor data $17_1$, $17_2$, $17_3$, ..., $17_n$ to at least one motion pattern $15_1$, $15_2$, $15_3$, ..., $15_n$, and since said motion patterns $15_1$, $15_2$, $15_3$, ..., $15_n$ may each be associated with one or more different zones $21_1$, $21_2$, $21_3$, ..., $21_n$ of the target surface 12, the probability values may indicate how probable it is, that the acquired at least one inertial sensor data $17_1$, $17_2$, $17_3$, ..., $17_n$ may correspond to one of the different zones $21_1$, $21_2$, $21_3$, ..., $21_n$ of the target surface 12. This is called the mapping of the at least one inertial sensor data $17_1$, $17_2$, $17_3$, ..., $17_n$ to at least one of the motion patterns $15_1$, $15_2$, $15_3$, ..., $15_n$.

Since each motion pattern $15_1$, $15_2$, $15_3$, ..., $15_n$ may be associated with one or more different zones $21_1$, $21_2$, $21_3$, ..., $21_n$ of the target surface 12, the mapping of the at least one inertial sensor data $17_1$, $17_2$, $17_3$, ... $17_n$ with the at least one motion pattern $15_1$, $15_2$, $15_3$, ..., $15_n$ indicates an estimation of the location of the movable treatment device 11 with respect to the one or more zones $21_1$, $21_2$, $21_3$, ... $21_n$ of the target surface 12. The location of the treatment device 11 may be estimated because the inventive location detection may be based on the above mentioned probability values in contrast to absolute valued geodata from a GPS, for instance.

In other words, the apparatus 10 may derive, from the neural network 18, an estimation in which zone $21_1$, $21_2$, $21_3$, ... $21_n$ of the target surface 12 the movable treatment device 11 is located by simply receiving sensor data $17_1$, $17_2$, $17_3$, ... $17_n$ and mapping said sensor data $17_1$, $17_2$, $17_3$, ..., $17_n$ to motion patterns $15_1$, $15_2$, $15_3$, ..., $15_n$ being associated with one or more zones $21_1$, $21_2$, $21_3$, ... $21_n$ of the target surface 12.

Thus, according to an embodiment, an output y(t) of the neural network 18 may comprise one or more probability values for the estimation of the location of the movable treatment device 11 with respect to the one or more zones $21_1$, $21_2$, $21_3$, ... $21_n$ of the target surface 12.

According to yet a further embodiment, the motion pattern recognition device 14 may be configured to determine from the at least one inertial sensor data $17_1$, $17_2$, $17_3$, ... $17_n$ a mutual movement of the movable treatment device 11 and the target surface 12, and to remove the determined movement of the target surface 12 from the determined movement of the movable treatment device 11.

For example the movable treatment device 11 may be a toothbrush and the target surface 12 may be a user's dentition. The user may turn his head while brushing his teeth. In this case the inertial sensor 13 would sense the mutual movement of the user's head and the toothbrush, since the toothbrush is moved together with the head. This may lead to a wrong motion detection, therefore to a wrong mapping, and finally to a wrong localization based on the mapping.

However, according to the above embodiment the sensed or determined movement of the user's head (target surface) 12 may be removed from the sensed mutual movement of the head and the toothbrush. In result only the desired movement of the toothbrush (treatment device) 11 remains. As will be described in further detail below, this movement of the user's head (target surface) 12 may be detected by a camera associated with the apparatus 10, where image and/or video output of the camera may be classified by neural network 18 (or by a separate learning network).

FIG. 8 shows a block diagram of an example of a method for performing a localization of a movable treatment device 11 relative to a target surface 12, wherein the movable treatment device 11 comprises an inertial sensor 13 and wherein the movable treatment device 11 is configured to treat the target surface 12.

In block 801 the method comprises a step of discriminating between two or more motion patterns $15_1$, $15_2$, $15_3$, ..., $15_n$ contained in a set 15 of motion patterns of the movable treatment device 11.

In block 802 the method comprises a step of receiving at least one inertial sensor data $17_1$, $17_2$, $17_3$, ... $17_n$ from the inertial sensor 13, the at least one inertial sensor data $17_1$, $17_2$, $17_3$, ..., $17_n$ representing a movement of the movable treatment device 11.

In block 803 the method comprises a step of receiving and processing by means of a neural network 18 the at least one inertial sensor data $17_1$, $17_2$, $17_3$, ..., $17_n$ and mapping/classifying the at least one inertial sensor data $17_1$, $17_2$, $17_3$, ..., $17_n$ to at least one motion pattern $15_1$, $15_2$, $15_3$, ..., $15_n$ contained in the set 15 of motion patterns, wherein said motion patterns $15_1$, $15_2$, $15_3$, ..., $15_n$ contained in the set 15 of motion patterns are each associated with one or more different zones $21_1$, $21_2$, $21_3$, ..., $21_n$ of the target surface 12 so that the mapping/classifying of the at least one inertial sensor data $17_1$, $17_2$, $17_3$, ..., $17_n$ with the at least one motion pattern $15_1$, $15_2$, $15_3$, ..., $15_n$ indicates an estimation of the location of the movable treatment device 11 with respect to the one or more zones $21_1$, $21_2$, $21_3$, ... $21_n$ of the target surface 12.

Figure 9:
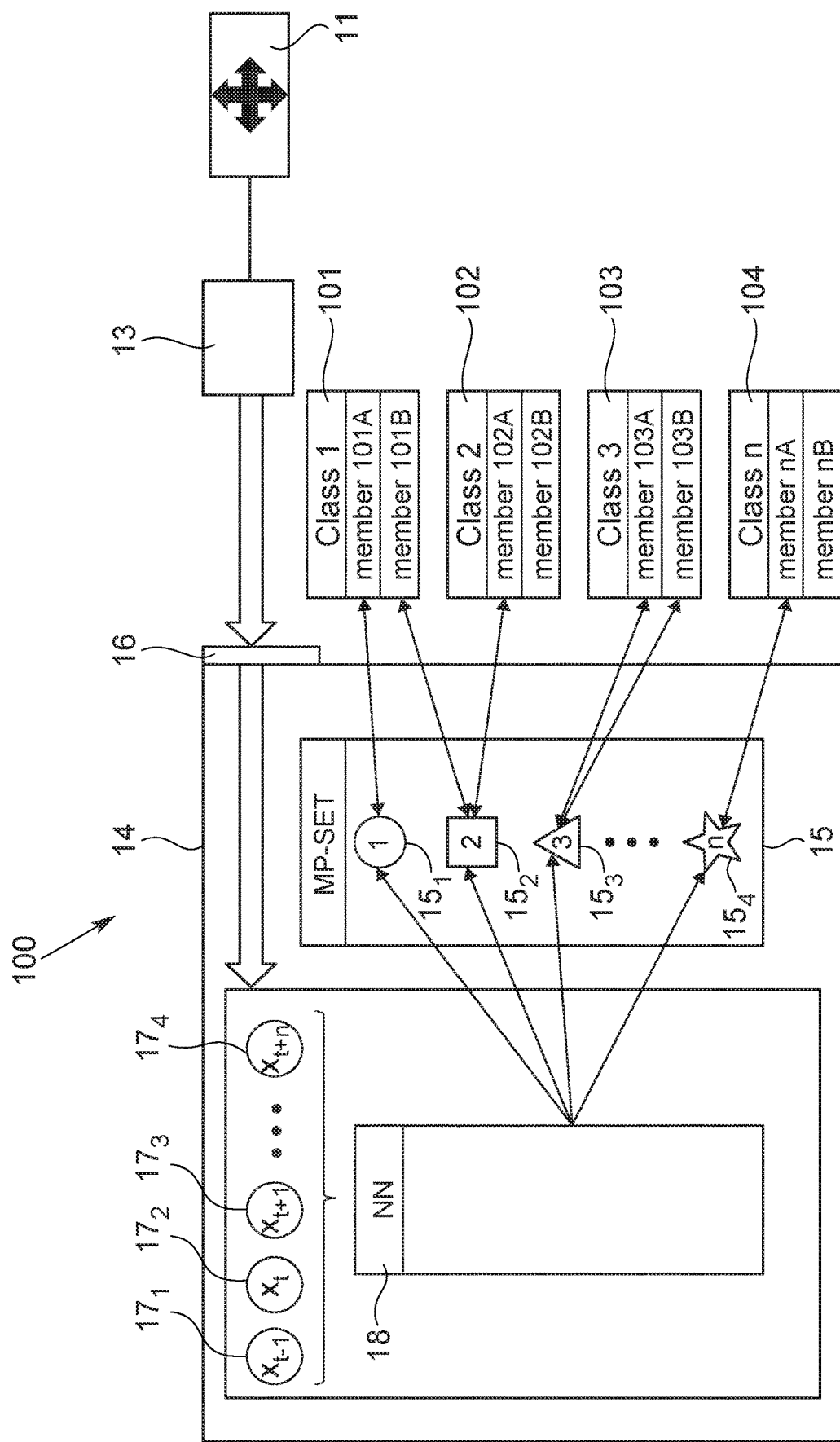
FIG. 9 shows a schematic block diagram of an apparatus according to an embodiment of the current disclosure.

FIG. 9 shows another exemplary apparatus 100 according to the current disclosure. The apparatus 100 may be similar to the above described apparatus 10. Furthermore, all of the features described above with respect to the apparatus 10 are combinable with the below described apparatus 100, and vice versa.

The apparatus 100 may vary from the apparatus 10 (c.f. FIG. 1) in that the motion patterns $15_1$, $15_2$, $15_3$, ..., $15_n$ may be mapped/classified to one or more class members 101A, 101B, ..., 104A, 104B of different classes 101, 102, 103, 104 instead of different zones $21_1$, $21_2$, $21_3$, ..., $21_n$ of a target surface 12.

Accordingly, the apparatus 100 is configured for classifying a motion of a movable personal appliance 11, also referred to herein as a moveable treatment device 11, comprising an inertial sensor 13. The apparatus 100 comprises a motion pattern recognition device 14 configured to discriminate between two or more motion patterns 151, 152, 153, ..., 15n contained in a set 15 of motion patterns of the movable personal appliance 11.

Furthermore, the apparatus 100 comprises an interface 16 for providing at least one inertial sensor data $17_1$, $17_2$, $17_3$, ..., $17_n$ from the inertial sensor 13 to the motion pattern recognition device 14, wherein the at least one inertial sensor data $17_1$, $17_2$, $17_3$, ..., 17n represents a motion of the movable personal appliance 11.

The motion pattern recognition device 14 comprises a neural network 18 that is configured to receive the at least one inertial sensor data $17_1$, $17_2$, $17_3$, ..., $17_n$ and to map/classify the at least one inertial sensor data $17_1$, $17_2$, $17_3$, ... $17_n$ to at least one motion pattern $15_1$, $15_2$, $15_3$, ..., $15_n$ contained in the set 15 of motion patterns, wherein the at least one mapped motion pattern $15_1$, $15_2$, $15_3$, ..., $15_n$ is associated with at least one class member 101A, 101B, 102A, 102B, 103A, 103B, 104A, 104B of one or more classes 101, 102, 103, 104 so that the at least one class member 101A, 101B, ..., 104A, 104B is selected based on the motion of the movable personal appliance 11.

In other words, the neural network 18 may map/classify the at least one inertial sensor data $17_1$, $17_2$, $17_3$, ..., $17_n$ to at least one motion pattern $15_1$, $15_2$, $15_3$, ..., $15_n$, e.g. in a way as previously described above with reference to FIGS. 1 to 8. Since the mapped motion patterns $15_1$, $15_2$, $15_3$, ..., $15_n$ may each be associated with at least one class member 101A, 101B, ..., 104A, 104B of one or more classes 101, 102, 103, 104, the at least one class member 101A, 101B, ..., 104A, 104B may be selected based on the at least one mapped motion pattern $15_1$, $15_2$, $15_3$, ..., $15_n$ of the movable personal appliance 11, i.e. based on the motion of the movable personal appliance 11.

The non-limiting example of FIG. 9 shows four classes 101, 102, 103, 104, wherein each class comprises two class members 101A, 101B, ..., nA, nB. However, there may be at least one class and each class may comprise at least two class members. There may also be more than two classes or even more than the exemplarily depicted four classes.

As can be seen in the example of FIG. 9, a first mapped/classified motion pattern $15_1$ may be associated with a class member 101A of the first class 101. An $n^{th}$ mapped/classified motion pattern 154 may be associated with a class member nB of the fourth class 104. A second mapped/classified motion pattern $15_2$ may be associated with two class members of different classes, for example with a class member 101B of the first class 101 and with a class member 102A of the second class 102. A third mapped/classified motion pattern 153 may be associated with two class members of the same class, for example with two class members 103A, 103B of the third class.

Generally at least one mapped/classified motion pattern $15_1$, $15_2$, $15_3$, ..., $15_n$ may be associated with at least one class member 101A, 101B, 102A, 102B, 103A, 103B, 104A, 104B of one or more classes 101, 102, 103, 104.

In the following, some examples of classes and class members will be described.

According to an embodiment, at least one class 101 of the one or more classes 101, 102, 103, 104 may comprise at least one class member 101A, wherein said one class 101 may represent a user group, and wherein said at least one class member 101A may represent at least one user of said user group, wherein the at least one mapped motion pattern $15_1$, $15_2$, $15_3$, ..., $15_n$ may be associated with the at least one class member 101A for identifying said at least one user based on the motion of the movable personal appliance 11.

In other words, one of the classes 101, 102, 103, 104 may represent a user group, i.e. a group of users using the movable personal appliance 11. The respective class may comprise at least one class member that may represent one particular user of said user group. For example, the first class 101 may represent a user group, wherein said user group may be a single household. In this example, the user group 101 may only contain one class member 101A, i.e. one person. The inventive apparatus 100 may be configured to identify said at least one user 101A simply based on the motion of the movable personal appliance 11. Thus, the inventive apparatus 100 may personalize any actions or interactions with said one identified user 101A, as will be described with some examples later.

According to a further embodiment, at least one class 101 of the one or more classes 101, 102, 103, 104 may comprise at least two class members 101A, 101B, wherein said one class 101 may represent a user group, and wherein said at least two class members 101A, 101B may represent at least two users of said user group, wherein the at least one mapped motion pattern $15_1$, $15_2$, $15_3$, ..., $15_n$ may be associated with one of said at least two class members 101A, 101B for identifying at least one user within the user group based on the motion of the movable personal appliance 11.

In other words, one of the classes 101, 102, 103, 104 may represent a user group, i.e. a group of users using the movable personal appliance 11. The respective class may comprise at least one class member that may represent one particular user of said user group. For example, the first class 101 may represent a user group, wherein said user group may be a family. The classes 101A, 101B of said class 101 may represent the family members. For example, the user group 101 may comprise one or more family members, wherein a first class member 101A may represent the mother of the family and a second class member 101B may represent a child of the family, for example.

The apparatus 100 may be configured to identify at least one user simply based on the motion of the movable personal appliance 11. This may be achieved if every user may use the 1 movable personal appliance 11 in a different or individual way.

For example, in an embodiment the movable personal appliance 11 may be a movable oral care device, such as a toothbrush, in particular an electric toothbrush. The movable oral care device may also be at least one of a dental floss, a plaque removing device, an ultrasound device and a waterjet device.

To take up the example above, the mother 101A may use the toothbrush 11 in a different way than the child 101B. The inertial sensor 13 of the toothbrush 11 may provide its inertial sensor data $17_1, 17_2, 17_3, \ldots, 17_n$ to the motion pattern recognition device 14 comprising the neural network 18. The neural network 18 may map/classify the inertial sensor data $17_1, 17_2, 17_3, \ldots, 17_n$ to at least one motion pattern $15_1, 15_2, 15_3, \ldots, 15_n$.

For example, as shown in FIG. 9, the mother may have a brushing style that corresponds to the first motion pattern $15_1$. This motion pattern $15_1$ may be associated with class member 101A that represents the mother. The child instead may have a different brushing style than the mother, for example a brushing style that corresponds to the second motion pattern $15_2$. This motion pattern $15_2$ may be associated with class member 101B that represents the child.

Thus, the apparatus 100 may identify a user of a user group simply based on the motion of the movable personal appliance 11. As mentioned above, the inventive apparatus 100 may personalize any action or interaction with the identified user.

According to an embodiment, the motion pattern recognition device 14 may be configured to select, based on the step of identifying said at least one user 101A, a user-specific motion pattern preset 115 comprising two or more user-specific motion patterns $115_1, 115_2, 115_3, \ldots, 115_n$ of the movable personal appliance 11 which are characteristic for said identified at least one user 101A.

Figure 10:
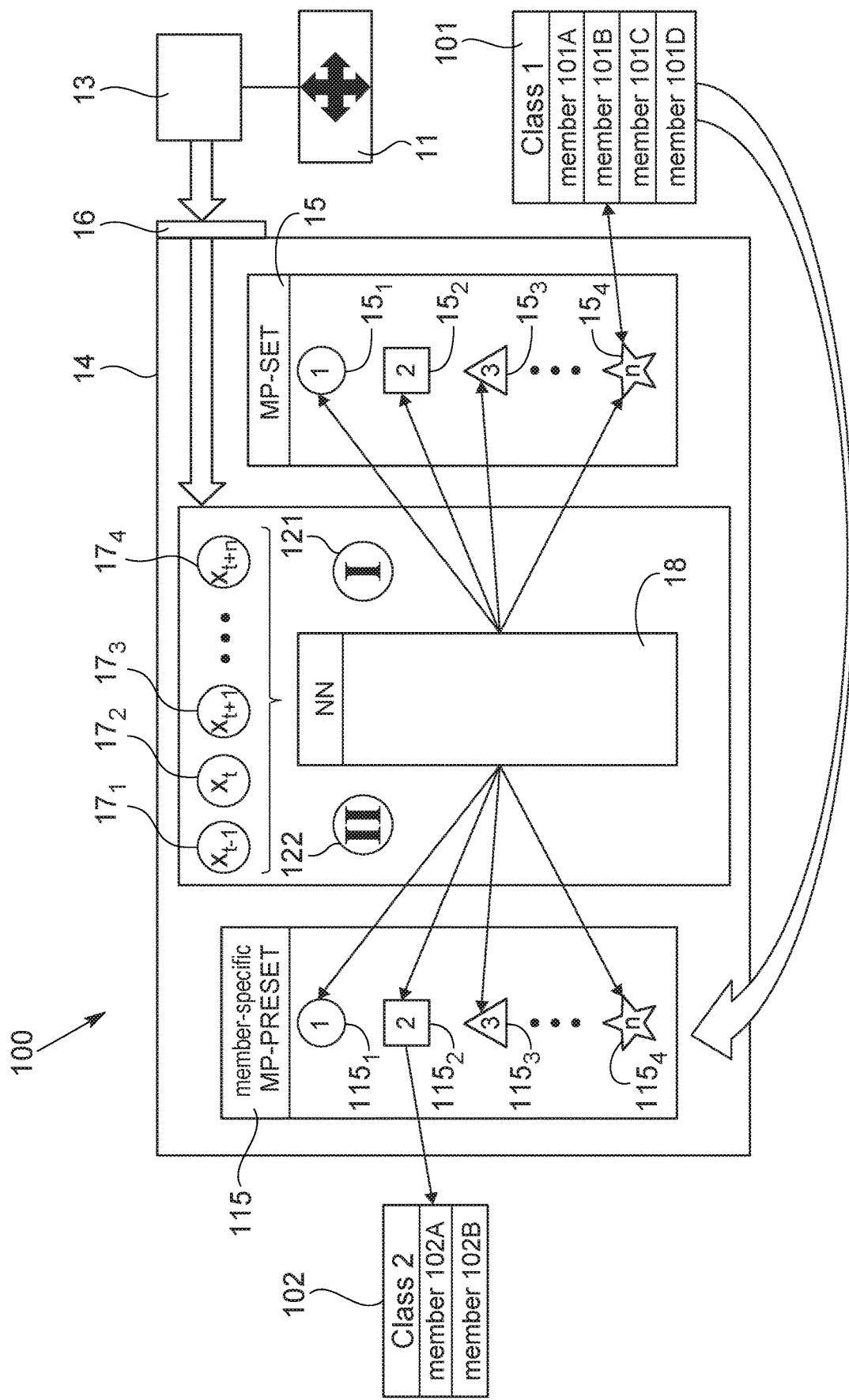
FIG. 10 shows a schematic block diagram of an apparatus according to a further embodiment of the current disclosure.

Such an example is shown in FIG. 10. This embodiment may also be referred to as a two-step process. In a first step 121, a user is identified. The identified user may have a user specific motion pattern preset 115 that has been individually trained by the neural network 18. In a second step 122 the neural network 18 uses the user specific motion patterns $115_1, 115_2, 115_3, \ldots, 115_n$ from the user-specific motion pattern preset 115. Thus, the inventive apparatus 100 may then act and interact with each identified user individually.

In FIG. 10 a first step 121 is shown in which the neural network 18 receives the at least one inertial sensor data $17_1, 17_2, 17_3, \ldots, 17_n$ and maps same to at least one of the motion patterns $15_1, 15_2, 15_3, \ldots, 15_n$ that are contained in the set 15 of motion patterns. The at least one mapped motion pattern, for example the nth notion pattern $15_4$, may be associated with a class member 101B of a first class 101. This procedure may correspond to the procedure as described above with reference to FIG. 9.

The class 101 may be a user group and the class member 101B may be a user of said user group. To take up the above example, the identified user 101B may be the child of the family. The apparatus 100 may have stored user specific motion patterns. That is, the identified user, i.e. the child 101B, may have its own individual user specific preset 115 of motion patterns $115_1, 115_2, 115_3, \ldots, 115_n$ stored in the apparatus 100. For any further actions following the identification in the first step 121, the motion pattern recognition device 14, and in particular the neural network 18, may use these user specific motion patterns $115_1, 115_2, 115_3, \ldots, 115_n$ belonging to the previously identified user.

Thus, the neural network 18 may select, after the step 121 of identifying said at least one user 101B, at least one user-specific motion pattern preset 115 comprising two or more user-specific motion patterns $115_1, 115_2, 115_3, \ldots, 115_n$ of the movable personal appliance 11 which are characteristic for said identified at least one user 101B.

Accordingly, in a second step 122 following the first step 121 of identifying the user, the neural network 18 may use the user specific preset 115 of user specific motion patterns $115_1, 115_2, 115_3, \ldots, 115_n$ in replacement of the set 15 of motion patterns $15_1, 15_2, 15_3, \ldots, 15_n$. That is, all of the herein described actions that can be executed by the apparatuses 10, 100 by exploiting the set 15 of motion patterns $15_1, 15_2, 15_3, \ldots, 15_n$ can also be executed individualized or personalized for each identified user by the apparatuses 10, 100 by exploiting the user specific preset 115 of motion patterns $115_1, 115_2, 115_3, \ldots, 115_n$ instead of the set 15 of motion patterns $15_1, 15_2, 15_3, \ldots, 15g$.

Thus, according to an embodiment the neural network 18 may be configured to replace, after the first step 121 of identifying said at least one user 101B, the set 15 of motion patterns by the selected user-specific motion pattern preset 115, and to replace the two or more motion patterns $15_1, 15_2, 15_3, \ldots, 15_n$ contained in the set 15 of motion patterns by the two or more user-specific motion patterns $115_1, 115_2, 115_3, \ldots, 115_n$ contained in the user specific motion pattern preset 115.

Figure 11:
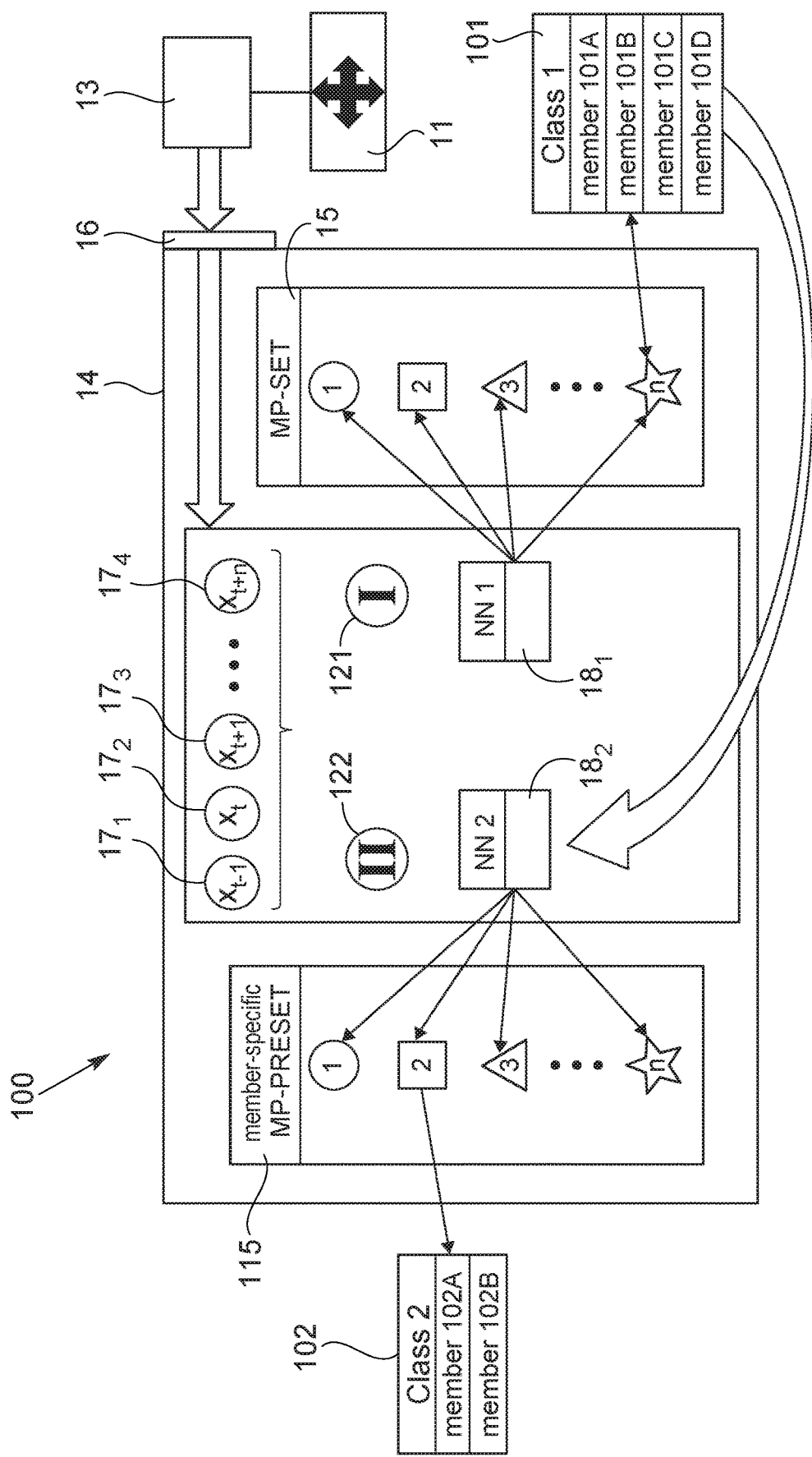
FIG. 11 shows a schematic block diagram of an apparatus according to a further embodiment of the current disclosure.

Additionally or alternatively, the apparatus 100 may comprise at least a second neural network. FIG. 11 shows such an example.

The example of the apparatus 100 of FIG. 11 may substantially correspond to the apparatus 100 of the example shown in FIG. 10. The apparatus of FIG. 11 differs from the apparatus of FIG. 10 in that the apparatus of FIG. 11 may comprise a second neural network 182.

As can be seen in FIG. 11, in a first step 121 a first neural network 181 may execute the actions as described above, for example identifying a user 101B of a user group 101. However, in a second step 122 the inertial sensor data $17_1, 17_2, 17_3, \ldots 17_n$ may be fed into said second neural network 182. The second neural network 182 may use the user specific preset 115 of motion patterns $115_1, 115_2, 115_3, \ldots, 115_n$ as described above.

In other words, after the first step 121 of identifying said at least one user 101B, the motion pattern recognition device 14 may use the second neural network 182, wherein the second neural network 182 may be configured to receive the at least one inertial sensor data $17_1, 17_2, 17_3, \ldots, 17_n$ and to map the at least one inertial sensor data $17_1, 17_2, 17_3, \ldots 17_n$ to at least one user specific motion pattern $115_1, 115_2, 115_3, \ldots, 115_n$ contained in the user specific preset 115 of motion patterns, wherein said user specific motion patterns $115_1, 115_2, 115_3, \ldots, 115_n$ are each associated with at least one class member 102A, 102B of one or more classes 101, . . . , 104 so that the at least one class member 102A, 102B is selected based on the motion of the movable personal appliance 11. In other words, the neural network 18 may be a user specifically trained neural network.

Accordingly, the motion pattern recognition device 14 may be configured to use the user specific preset 115 of user specific motion patterns $115_1, 115_2, 115_3, \ldots, 115_n$ for user-specifically classifying the motion of the personal appliance 11 by means of the at least one inertial sensor data $17_1, 17_2, 17_3, \ldots, 17_n$.

As shown in the examples of FIGS. 10 and 11, the apparatus 100 may comprise at least one class 102 for classifying purposes in the second step 122. However, the apparatus 100 may comprise more than one class, as shown in the example of FIG. 9, in the second step 122.

In said second step 122, for example after having identified a particular user in the first step 121, different actions may be performed by the personal appliance 11. For example, the personal appliance 11 may change its operation mode based on the identified user. For example, the personal appliance 11 may be electrical driven and it may comprise a motor (See FIGS. 15 & 16), wherein the personal appliance 11 may change one or more motor specific characteristics, such as frequency, amplitude or pulsation, based on the identified user. Additionally or alternatively, the personal appliance 11 may comprise one or more elements for communicating with or providing feedback to a user, for example a visual element, such as a light, e.g. a LED, or a haptical element, such as a vibrational motor. For example, the personal appliance 11 may change a user experience based on the identified user by changing the operation mode of said elements for communicating, for instance by changing LED lights to a different color or by providing differently pulsed feedback by the vibrational motor, based on the identified user.

Additionally or alternatively to identifying a particular user of a user group, for example a family member of a family, the apparatus 100 may be configured to identify a particular user type. For example, if the personal appliance 11 was a toothbrush, some people start brushing their teeth with their front teeth or incisors while some other people may start brushing their teeth with their back teeth or molars. In a further example, if the personal appliance was a razor, some people may shave with the grain while some other people may shave against the grain Summarizing a user type may be a type of user who uses the personal appliance 11 in a particular way. There may be two or more users that can be clustered into groups of user types. The previously described example of user identification instead identifies each user individually.

According to an embodiment for identifying user types, at least one class 104 of the one or more classes 101, 102, 103, 104 may comprise at least two class members nA, nB, wherein said one class 104 may represent a user type of the movable personal appliance 11, wherein a first class member nA may represent a first user type of the movable personal appliance 11 and wherein a second class member nB may represent a second user type of the movable personal appliance 11, wherein the at least one mapped motion pattern $15_1$, $15_2$, $15_3$, ..., $15_n$ may be associated with either the first or the second class member nA, nB for identifying a user type of the movable personal appliance 11 based on the motion of the movable personal appliance 11.

According to a further embodiment, the motion pattern recognition device 14 may be configured to select, after the step of identifying said user type, a user type specific motion pattern preset 115 comprising two or more user type specific motion patterns $115_1$, $115_2$, $115_3$, ..., $115_n$ of the movable personal appliance 11 which are characteristic for said identified user type, and wherein the neural network 18 may be configured to replace, after the step of identifying said user type, the set 15 of motion patterns by the selected user type specific motion pattern preset 115 and to replace the two or more motion patterns $15_1$, $15_2$, $15_3$, ..., $15n$ contained in the set 15 of motion patterns by the two or more user type specific motion patterns $115_1$, $115_2$, $115_3$, ..., $115_n$.

Everything that has been explained above with respect to the user specific preset 115 of user specific motion patterns $115_1$, $115_2$, $115_3$, ..., $115_n$ also holds true for the user type specific preset 115 of user type specific motion patterns $115_1$, $115_2$, $115_3$, ..., $115_n$.

As mentioned above, the identified user types may be clustered into a cluster or group of user types. Therefore, the apparatus 100 may perform a cluster analysis in which a user may use the personal appliance 11 for a predetermined number of times before this user is clustered into a particular user type group. For example, a user may use its razor five times on five subsequent days. On four out of the five days the user may shave against the grain. Thus, after the fifth day the apparatus 100 may cluster this user into a user type group in which all users shaving against the grain are clustered.

The cluster analysis may also be performed at shorter time intervals, i.e. switching the toothbrush 11 on and off may be done directly successively. For example the user may switch on his electric toothbrush 11 a first time, switch it off, and switch it on a second time to restart the toothbrush 11 again. At the time of restarting the toothbrush 11, the inventive apparatus 100, and in particular the neural network 18, may also be restarted. When the toothbrush 11 is switched on, it may collect information for the cluster analysis. However, at least the neural network 18 shall restart every time before new information for the cluster analysis is collected. Summarizing, the apparatus 100 may repeatedly (e.g. five times) perform the cluster analysis before finally clustering the user into a particular user type group.

After the user has been clustered into a particular user type specific group, the neural network 18 may use the associated user type specific preset 115 of user type specific motion patterns $115_1$, $115_2$, $115_3$, ..., $115_n$.

According to such an embodiment, the motion pattern recognition device 14 may be configured to repeatedly perform a cluster analysis for a predetermined number of times, wherein in each said cluster analysis the neural network 18 may be configured to restart and to perform, after the restart, the step of receiving the at least one inertial sensor data $17_1$, $17_2$, $17_3$, ... $17_n$ and to map the at least one inertial sensor data $17_1$, $17_2$, $17_3$, ... $17_n$ to at least one motion pattern $15_1$, $15_2$, $15_3$, ..., $15_n$ contained in the set 15 of motion patterns, and wherein the neural network 18 may be configured to select the user type specific motion pattern preset 115 after performing the cluster analysis for the predetermined number of times.

The inventive apparatus 100 may provide even more scenarios for classifying a motion of the movable personal appliance 11. Therefore, reference shall be made to FIG. 9 again.

According to an embodiment, at least one class 102 of the one or more classes 101, 102, 103, 104 may comprise at least two class members 102A, 102B, wherein said one class 102 may represent a handling evaluation of the movable personal appliance 11, wherein a first class member 102A may represent a correct handling of the movable personal appliance 11 and wherein a second class member 102B may represent a wrong handling of the movable personal appliance 11, wherein the at least one mapped motion pattern $15_1$, $15_2$, $15_3$, ..., $15_n$ may be associated with either the first or the second class member 102A, 102B for evaluating the handling of the movable personal appliance 11 based on the motion of the movable personal appliance 11.

In other words, the apparatus 100 may be configured to check whether a user of the movable personal appliance 11 may use the movable personal appliance 11 correctly or not. Of course, said one class 102 representing the handling evaluation may also be used as a class in the second step 122 of the above described two-step procedures of FIGS. 10 and 11, e.g. after identifying a user and/or a user type.

According to a further embodiment at least one class 103 of the one or more classes 101, 102, 103, 104 may comprise at least two class members 103A, 103B, wherein said one class 103 may represent a quality of motion execution of the movable personal appliance 11, wherein a first class member 103A may represent a good motion execution of the movable personal appliance 11 and wherein a second class member 103B may represent a bad motion execution of the movable personal appliance 11, wherein the at least one mapped motion pattern $15_1$, $15_2$, $15_3$, ..., $15n$ may be associated with either the first or the second class member 103A, 103B for evaluating a quality of motion execution of the movable personal appliance 11 based on the motion of the movable personal appliance 11.

In other words, the apparatus 100 may be configured to check whether a user of the movable personal appliance 11 may use the movable personal appliance 11 in a good way or in a bad way. A good way may be a way of performing the motion of the movable personal appliance as intended, while a bad way may be a way of performing the motion of the movable personal appliance 11 as not intended. For example, if the personal appliance 11 was a toothbrush, then the apparatus may check whether the user may have a good or a bad brushing technique.

Of course, said one class 103 representing the quality of motion execution may also be used as a class in the second step 122 of the above described two-step procedures of FIGS. 10 and 11, e.g. after identifying a user and/or a user type.

Yet a further embodiment of the apparatus 100 may be similar to the apparatus 10 as described with reference to FIGS. 1 to 8.

According to such an embodiment, at least one class 104 of the one or more classes 101, 102, 103, 104 may comprise at least two class members nA, nB, wherein said one class 104 may represent a location of the movable personal appliance 11 with respect to a target surface 12, wherein a first class member nA may represent a first location zone 211 of the movable personal appliance 11 with respect to the target surface 12 and wherein a second class member nB may represent a second location zone 212 of the movable personal appliance 11 with respect to the target surface 12, wherein the at least one mapped motion pattern $15_1$, $15_2$, $15_3$, ..., $15n$ may be associated with at least one of the first and the second class members nA, nB for localizing the movable personal appliance 11 within at least one of the first and the second location zones 211, 212 based on the motion of the movable personal appliance 11.

In other words, the one class 104 may represent a target surface 12. The class members nA, nB of said one class 104 may represent different zones 211, 212 of said target surface 12. Accordingly, the localization of the movable personal appliance 11 with respect to the target surface 12 may be executed by the apparatus 10 in the same or at least a similar fashion as described above with respect to the apparatus 10 with reference to FIGS. 1 to 8.

Of course, said one class 104 representing the location of the movable personal appliance 11 with respect to the target surface 12 may also be used as a class in the second step 122 of the above described two-step procedures of FIGS. 10 and 11, e.g. after identifying a user and/or a user type.

According to an embodiment, at least one class 101 of the one or more classes 101, 102, 103, 104 may comprise at least one class member 101A, wherein said one class 101 may represent an appliance type (e.g. shaving appliance, dental appliance, broom), and wherein said at least one class member 101A may represent at least one specific appliance in the appliance type group, wherein the at least one mapped motion pattern $15_1$, $15_2$, $15_3$, ..., $15_n$ may be associated with the at least one class member 101A for identifying said at least one specific appliance based on the motion of the movable personal appliance 11.

The neural network 18 of the apparatus 100 may comprise the same or similar features as the neural network 18 of the apparatus 10 that has been described with reference to FIGS. 4 to 7. Thus, it shall be briefly referred to FIG. 7 again.

According to an embodiment, the neural network 18 may comprise at least a first and a second layer 71, 72, wherein each layer may comprise a neural unit 60, 70, wherein at a first time instant t the at least one inertial sensor data Xt $17_2$ may be input into the neural unit 60 of the first layer 71, and wherein at a subsequent second time instant t+1 a second inertial sensor data Xt+1 and at least one output ht 46 of the previous first time instant t may be input into the neural unit 60 of the first layer 71, and/or wherein at the subsequent second time instant t+1 the at least one output ht 46 of the first time instant t may be input into the neural unit 71 of the second layer 72.

Everything that has been described above with respect to any features of the neural network 18 of the apparatus 10 as shown in FIGS. 4 to 7 also holds true for the neural network 18 of the apparatus 100 as described with reference to FIGS. 9 to 11.

FIG. 12 shows a block diagram of an inventive method for classifying a motion of a movable personal appliance 11 that comprises an inertial sensor 13.

In block 1201 the method comprises a step of discriminating between two or more motion patterns $15_1$, $15_2$, $15_3$, ..., $15_n$ contained in a set 15 of motion patterns of the movable personal appliance 11.

In block 1202 the method comprises a step of providing at least one inertial sensor data $17_1$, $17_2$, $17_3$, ..., $17_n$ from the inertial sensor 13 to the motion pattern recognition device 14, the at least one inertial sensor data $17_1$, $17_2$, $17_3$, ..., $17_n$ representing a motion of the movable personal appliance 11.

In Block 1203 the method comprises a step of receiving and processing, by means of a neural network 18, the at least one inertial sensor data $17_1$, $17_2$, $17_3$, ..., $17_n$ and mapping the at least one inertial sensor data $17_1$, $17_2$, $17_3$, ..., $17_n$ to at least one motion pattern $15_1$, $15_2$, $15_3$, ..., $15_n$ contained in the set 15 of motion patterns, wherein the at least one mapped motion pattern $15_1$, $15_2$, $15_3$, ..., $15_n$ is associated with at least one class member 101A, 101B, 102A, 102B, nA, nB of at least one class 101, 102, 103, 104 so that the at least one class member 101A, 101B, 102A, 102B, nA, nB is selected based on the motion of the movable personal appliance 11.

According to yet a further example of the apparatus 10, 100 the movable treatment device 11 may be a personal grooming appliance and the target surface 12 may be a body portion to be treated by the movable treatment device 11.

According to yet a further example of the inventive apparatus 10, 100 the movable treatment device 11 or the movable personal appliance 11 may comprise a pressure sensor for sensing a pressure applied onto a target zone by the personal appliance and/or a load sensor for sensing a motor load of a motor that may drive the personal appliance. Respective sensor data of the pressure sensor and/or the load sensor may be fed as input into the neural unit 18, in addition or alternatively to the at least one inertial sensor data $17_1$, $17_2$, $17_3$, ..., $17n$.

According to yet a further example of the inventive apparatus 10, the apparatus 10 may comprise an output interface for outputting to a user the one or more zones $21_1$, $21_2$, $21_3$, ... $21_n$ of the target surface 12 in which the movable treatment device 11 is located.

According to yet a further example of the inventive apparatus 100, the apparatus 100 may comprise an output interface for outputting information to a user, said information being related to the one or more classes 101, 102, 103, 104 and/or to the one or more class members 101A, 101B, . . . , nA, nB of the one or more classes 101, 102, 103, 104.

In each of the herein described embodiments, sensor data $17_1, 17_2, 17_3, \ldots, 17n$ can be stored on the movable personal appliance or treatment device 11 and later on can be fed into the apparatus 10, 100, in a way as described above. Any post processing of this stored sensor data $17_1, 17_2, 17_3, \ldots, 17_n$ into different zones or classes may be used to show a consumer or user on a dashboard how well and what zones they covered, what they forgot, what was in target vs out of target. This data may be shown as one usage or aggregated uses over time (i.e. show the consumer or user a simple dashboard of how they have been brushing over the week).

The following features may also be included:

Attention mechanism (add on to the RNN)

Prefiltering work

Removing head position dependency (looking at linear accl)

Dynamic time warping for user ID (finger print)

Local high freq sampling and 8 bit FFT to diff lingual and buccal (based on cheek damping of signal—this would be done by simple on device classifier followed by raw signal+device classifier into RNN Not only train a position predictor, but also train a "brushing correctly vs not"

Figure 13:
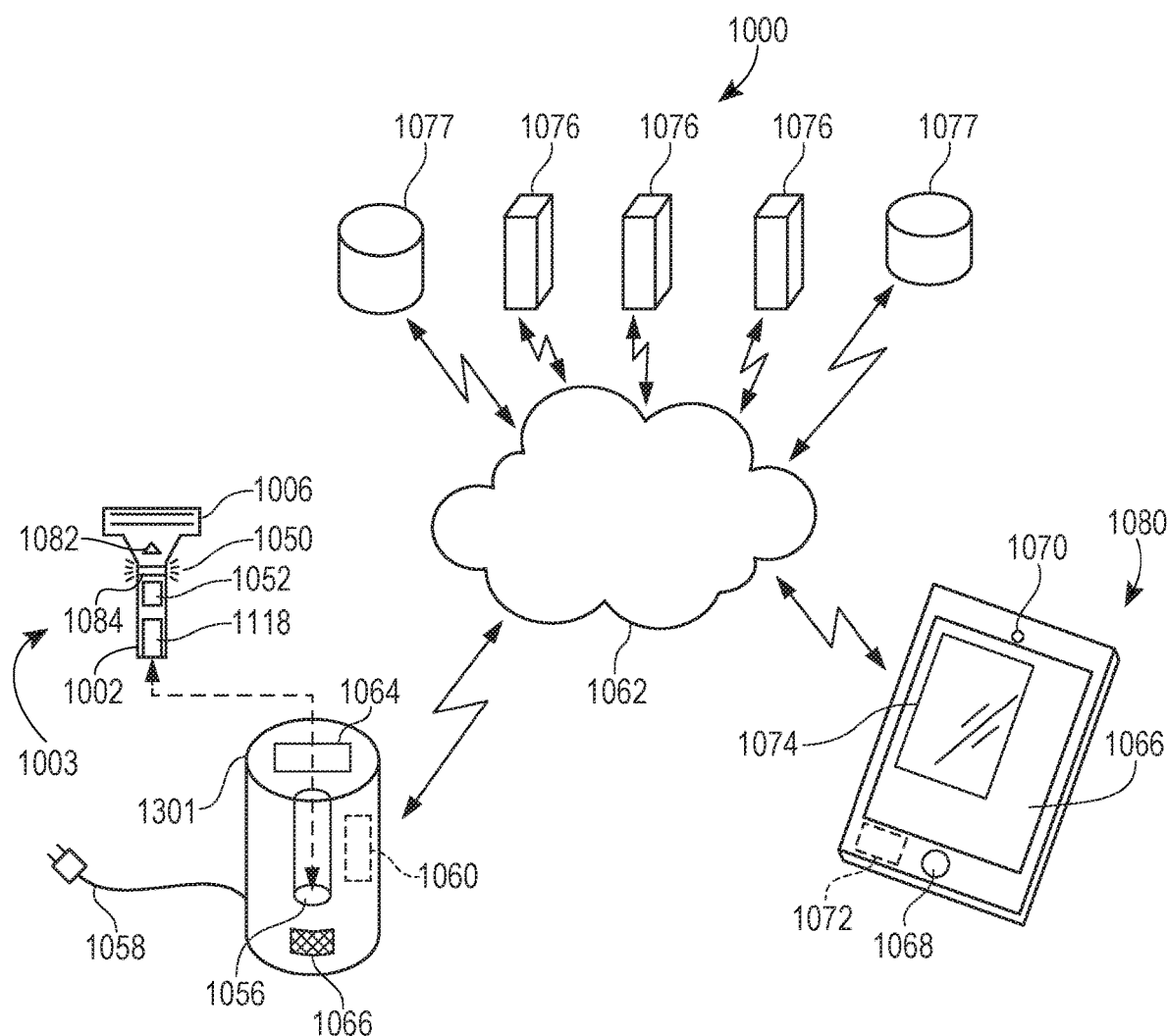

Doing cluster analysis (have user brush 1-5 times before placing them into a bucket) to put user in a defined space that uses a custom trained RNN for that type of user FIG. 13 discloses an example networked appliance system 1000 according to the current disclosure. The networked appliance system includes a grooming appliance 1003 which is illustrated in this example as a razor appliance. But the appliance may be any grooming appliance, household appliance or treatment device 11 disclosed herein. In the current example, the razor appliance 1003 includes a grooming implement such as a removable razor cartridge 1006, a razor handle 1002, an internal power source 1118, an optional multi-color LED display 1050, and an optional camera 1082.

As discussed above and herein, the razor appliance 1003 may include a plurality of internal sensors such as motion sensor(s), orientation sensor(s), cartridge ejection sensor(s), new cartridge detection sensors, and/or pressure sensor(s) associated with the handle 1002 and/or razor cartridge 1006. The shaving appliance 1003 may also include an appliance circuit 1052 connected to receive (via a data connection) sensor signals from the plurality of sensors contained within the razor appliance 1003. In the current embodiment, the network appliance system 1000 also includes a base station 1301, where the base station includes a seat 1056 for receiving and engaging with the handle 1002 of the razor appliance 1003. In the current embodiment, the base station 1301 may be powered by electricity via an electric cord 1058 that may be plugged into a standard electrical outlet. The seat 1056 may include electrodes (not shown) that are adapted to engage with and/or mate with corresponding electrodes (again not shown) on the razor appliance handle 1002. Through such electrodes the base station 1301 may provide power to charge the power source (such as a rechargeable battery) 1118 in the razor appliance 1003 and/or may provide an electrical connection for the transfer of data signals from the sensor circuit 1052 within the razor handle 1002 to a base station circuit 1060 residing within the base station 1301. It is also within the scope of the current disclosure that power may be provided from the base station 1052 to the razor's power source 1118 by a non-connected capacitive coupling as known in the art, or any other wireless mechanisms that are known for wirelessly/contactless transferring power from a first power source to a rechargeable power source. It is also within the scope of the current disclosure that the power source 1118 may be removable, such as disposable batteries and/or rechargeable batteries that are charged by something other than the base station 1301. Further, it is within the scope of the current disclosure that data transmitted/received between the razor 1003 and the base station 1301 may be via wireless data connection, such as a Bluetooth connection and the like. It is also within the scope of the current disclosure that some or all of the mechanisms, circuitry and/or functionality of the base station 1301 as described herein can reside within razor 1003. It will be appreciated that, while the base station 1301 is described in this example as associated with the razor 1003, similar base stations and base station functionalities may also be associated with other appliances disclosed herein.

In the current embodiment, the base station 1301 includes base station circuitry 1060 that includes processor(s) and corresponding circuitry for receiving the sensor signals (and/or information derived from the sensor signals) and converting the sensor signals/information into associated analysis/mapping/classification information as described herein. The base station circuitry 1060, in the current embodiment, also includes a network circuitry for a wireless data communication (e.g., such as a cellular and/or WiFi connection) with a computer network 1062 such as a cellular network and/or an internet network. The base station 1301 may also include a visual display 1064, such as an LCD display and/or a similar text or image display device as known to those of ordinary skill, where such display device 1064 may be controlled by the base station circuitry 1060. The base station 1301 may also include a sound actuator 1066 also controlled by the base station circuitry 1060, where the sound actuator 1066 may include a speaker or similar sound-making component.

The networked shaving appliance system 1000 also includes a computerized and networked user interface device 1080. The computerized and networked user interface device 1080 can be in the form of a smart phone, a tablet computer, personal assistant device, a laptop or desktop computer, smart display, smart mirror, a computerized wearable appliance such as a smart watch or smart glasses, and the like. The computerized and networked user interface device 1080 may include a display 1066, and a user input device such as a cursor control device 1068 (or a touch screen or a voice activated control, or a motion sensor, or an eye movement sensor and the like as are readily available to the art), a camera 1070 and associated processing circuitry 1072. The computerized and networked user interface device 1080 may operate to perform various software applications such as a computerized tool which may be in the form of a personal application 1073 (see FIGS. 15 & 16) associated with the appliance 11 as will be discussed in further detail herein. In the current embodiment, the application 1073 is a personal shaving application and may include a graphical user interface 1074, which may be displayed on the display screen 1066 and controlled and/or receive user input therein from the user input devices such as the cursor-controlled device 1068 and/or the touch screen. The user device circuitry 1072 may include a network circuit for connecting wirelessly with the computer network 1062 for the purpose of receiving and/or transmitting data over the computer network 1062.

As also illustrated in FIG. 13, the computer network 1062 may have various computer servers and/or distributed computing devices (collectively labeled as 1076) also accessible thereto and may additionally include various data storage devices 1077 operatively coupled by a data connection thereto. For example, the software application 1073 may include operations being performed on one or more of the computer servers/devices 1076 and/or on the device circuitry 1072. Likewise, data storage associated with the software application 1073 may be within one or more of the data storage devices 1077 and/or on the device circuitry 1072.

At a very high level, one or more of the appliance circuit 1052, base station circuit 1060, user device circuitry 1072 and/or processors associated with the distributed computing environment 1076 comprise a sensor circuit for receiving the sensor signals from the razor appliance 1003 and for analyzing/mapping/classifying the sensor signals as described herein. Likewise, again at a very high level, one or more of the appliance circuit 1052, base station circuit 1060, user device circuitry 1072 and/or processors associated with the distributed computing environment 1076 comprise an image processing circuit for receiving the image data from the camera 1082 and/or 1070 and for analyzing/mapping/classifying the image data as described herein. This analysis, mapping and/or classification information will also be communicated over the computer network 1062 so that a computerized tool which may be in the form of the software application 1073 operating on the networked user interface device 1080 may receive the analysis, mapping and/or classification information (or at least portions thereof) associated with a user of the computerized device 1080 from the network 1062. The computerized tool in the form of the software application 1073 may also be configured to receive user profile data information from the user via the graphical user interface 1074 provided by the software application 1073. Further, the software application 1073 may process the analysis, mapping and/or classification information received from the computer network 1062 with the user profile data provided by the user through the software application to generate user feedback information associated with the user's experience with the appliance 11 (razor 1003 in this example) as described herein; and then finally, communicate that user feedback information to the user via the graphical user interface 1074 provided by the computerized tool as also described herein and/or via the LED's 1050 on the razor 1003, and/or via the visual display 1064 on the base station, and/or via the sound actuator 1066 on the base station.

Figure 14:
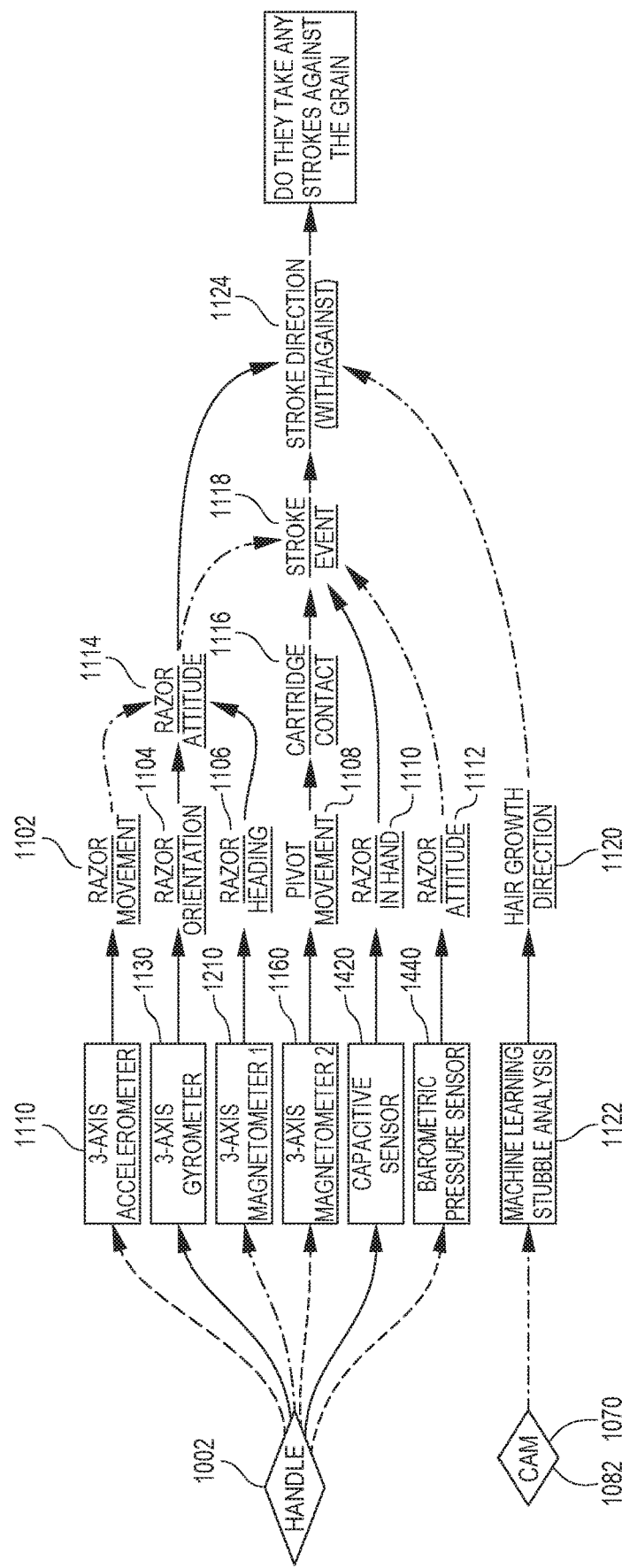
FIG. 14 is a flow diagram representation of a decision tree according to an embodiment of the current disclosure.

As shown in FIG. 14, specific examples of measurement information or shave event information for the razor 1003 may include (without limitation) razor movement information 1102 based upon acceleration in X, Y and Z directions derived from sensor data received form a 3-axis accelerometer 1110; razor orientation information 1104 based upon angle information derived from sensor signals received from a 3-axis gyro meter 1130; razor heading information 1106 based upon relationship with magnetic north derived from sensor signals received from a 3-axis magnetometer 1210; cartridge pivot movement information 1108 (also cartridge presence, cartridge contact and/or trimmer contact) based upon relationship of a magnet with respect to a pivot plunger derived from sensor signals received from a 3-axis magnetometer 1160; razor-in-hand information (information corresponding to a user gripping the handle 1002) 1110 based upon barometric pressure derived from sensor signals received from the capacitive sensor 1420; and razor attitude information 1112 derived from sensor signals received from the barometric pressure sensor 1440.

As also shown in FIG. 14, razor attitude information 1114 can be derived from a combination of the razor movement information 1102, razor orientation information 1104 and razor heading information 1106. Cartridge contact information 1116 can be derived from pivot movement information 1108. Stroke event information can be derived from a combination of the razor attitude information 1114, razor contact information 1116, razor-in-hand information 1110 and razor attitude information 1112.

As further shown in FIG. 14, the measurement and shave event information may also include image information provided by cameras and associated analysis, mapping and/or classification. For example, as will be described in further detail below, hair growth direction information 1120 may be provided by image information received through the camera 1082/1070 and through a stubble analysis 1122 performed on the image information using appropriate computer learning or statistical analyzers, mapper and/or classifiers described herein. Consequently, relative stroke direction information 1124 (which determines whether or not the stroke directions are with or against the direction of hair growth on the user's face) can be derived from a combination of razor attitude information 1114, stroke event information 1118 and the hair growth direction information 1120 provided by the image analysis. Similarly, over-stroke information or over-strokes with/against the grain can be determined based upon a combination of sensor readings taken from a plurality of the same sensors and image information as used for shave direction information and/or relative shave direction information.

Additional sensors, as discussed herein, may include thermistors for sensing handle operating temperature and/or in-handle temperature; capacitive sensors for sensing razor-in-hand; multi-capacitance sensors for sensing grip positions; clocks for sensing time; acoustic sensors for sensing shave performance (such as with or against grain) and the like.

Another aspect to the current disclosure is that the shave event information can be cumulative shave event information starting at a time with the system senses or is informed that a new shaving cartridge 1006 is attached to the razor 1003. New cartridge determination may be provided by receiving sensor signals associated with a cartridge eject button on the razor appliance 1003. Similarly, new cartridge determination information may be provided by having a new-cartridge sensor becoming active upon the cartridge ejections occurring (such as a mechanical switch being set for activation when a cartridge is ejected), where the new-cartridge sensor may be then actuated when the new cartridge is inserted. New cartridge information may also be manually indicated by the user such as through the software application 1073 or by the user pressing a reset button (or the like), for example, on the base station 1301. Additionally, new cartridge information may be detected by the razor appliance 1003 by detecting a unique I.D. for each razor cartridge that is attached to the handle 1002. For example, a unique I.D. can be a barcode on the cartridge sensed by an associated barcode reader on the handle; can be an RFID tag on the cartridge sensed by an associated RFID reader on the handle; can be an I.D. on the cartridge communicated to the handle by magnetic, electric or capacitive data communication; can be a physical I.D. such as a physical key on the cartridge 1006 that is sensed by the handle 1002; and so forth. Essentially, any known manner for the appliance 1003 or system 1000 to detect or be notified when a new razor cartridge 1006 is coupled to the handle 1002 (the new cartridge event) will begin the collection point for cumulative shave event data where that cumulative shave event data will be thereafter associated with the age of the new razor cartridge 1006. This cumulative shave event information can be used to calculate or estimate, for example, the sharpness of the associated blades contained within the cartridge 1006.

The systems and methods herein may include training one or more convolutional neural networks ("CNN") for determining the method of treating a target surface 12. The CNN can be used to identify target surfaces 12, treatment implements 11 and practitioner information relevant to the treatment method determined by the CNN. The CNN may utilize training images and/or audio data to train the convolutional neural network and may receive one or more training images or audio files to be utilized by the CNN to determine elements that define surface types, treatment implements, and practitioners. Once the CNN is trained, a camera 22 may capture an image (e.g., a digital image) of the target surface, implement, practitioner, for analysis by the CNN. The camera 22 may then provide image data 23 for analysis, mapping and/or classification as described herein. The analysis of the captured image data 23 may include a determination of the target surface 12 type, target surface 12 condition, target surface diagnosis, implement 11 type, user information as well as treatment method, additional relevant treatment products and treatment regimen information. The CNN and RNN structures may be used in sequence or in parallel to evaluate the data and determine a surface.

The image capture logic of the camera 22 and the software tool in the form of a computer application 1073 may include and/or utilize software components, hardware circuitry, firmware, and/or other computing infrastructure, as described herein. As described in more detail below, the image capture logic may facilitate capturing, storing, preprocessing, analyzing, transferring, and/or performing other functions on a digital image data 23. The application 1073 may be configured for providing one or more user interfaces 1074 to the user, which may include questions, options, and the like.

Features detected by the analysis/mapping/classifying system may include edges, shapes, colors, which may be used to identify age, gender, emotion, skin type, hair type, floor type, fabric type, tooth color, skin color, pimples/acne, redness, shine of skin & hair. Products/Devices—toothbrushes, comb, hair brush, ProX, razors, grooming devices, Swiffer, beauty/cosmetic device. Accordingly, the remote processing servers and/or computers 1076 include a memory component 1077, which stores training logic and analyzing logic. The training logic may facilitate creation and/or training of the CNN, and thus may facilitate creation of and/or operation of the convolutional neural network. The analyzing logic may cause the processing servers and/or computers 1076 to receive data from the mobile computing device 1080 (or other computing device) and process the received data for providing a treatment product recommendation, etc through the user interface 1074.

A training computer or server 1076 may be coupled to the network 1062 to facilitate training of the CNN. For example, a trainer may provide one or more images to the CNN via the training computer or server 1076. The trainer may also provide information and other instructions to inform the CNN which assessments are correct and which assessments are not correct. Based on the input from the trainer, the CNN may automatically adapt, as described in more detail below.

It should also be understood that while the training computer or server 1076 is described as performing the convolutional neural network processing, this is merely an example. RNNs or multi-layer-perceptron (MLP) may be used as alternative network architectures that and applied to video or other digital data including audio data. Any of these networks can be used since they are capable of analyzing, mapping and/or classifying video and/or sensor information. The convolutional neural network processing may be performed by any suitable computing device, as desired.

The present system may include a convolutional neural network ("CNN") that functions as a surface treatment expert system. For example, a CNN may be stored as logic in the memory component of a computing device. The CNN may be configured to receive a training image (or a plurality of training images) and take raw image pixels from the training image as input and automatically learn feature extractors that are relevant for determining surface, implement, and practitioner types from a captured digital image. Recent advances in a machine learning technique called deep learning have resulted in breakthrough performance in the realm of neural networks, such as is described in U.S. Pat. No. 8,582,807. Deep-learning-type neural networks utilize a plurality of layers inspired by the human visual cortex.

The CNN may be trained using predefined features and/or auto-learned features. After the CNN is trained, it may be used to determine surface treatment options from a captured image of the user from the learned features. In some instances, the CNN can learn to identify important features in an image through a process called supervised learning. Supervised learning generally means that the CNN is trained by analyzing examples of images in which the surface treatment options have been pre-defined. Depending on the accuracy that is desired, the number of training images may vary from a few images to a continuous input of images to provide for continuous training. Regardless, after training, the CNN learns key features for predicting the treatment method accurately for a wide range of surface types.

The CNN may include a plurality of stages. A first stage may include preprocessing and a second stage may include convolutional neural network training. During preprocessing, one or more features common to most scenarios and users, ("anchor features"), in a received image may be detected. The detection may be made based on edge detection, shape detection, and/or similar detection mechanisms, as are known. Based on the location of the anchor feature(s), the images may be scaled and rotated to make the image substantially level and with the anchor feature(s) arranged in a predetermined position in the final image. By doing this, the training images may be consistently aligned, thus providing more consistent results. The image may then be cropped to a predetermined area of pixels as input for further processing.

During preprocessing, data augmentation may also be performed to create additional samples from the training images. For example, the input image may be randomly enlarged and/or shrunk, randomly rotated in a clockwise direction and/or in a counter clockwise direction, randomly cropped, and/or randomly changed with regard to saturation and/or exposure. In some instances, the input image may be subjected to random vertical dropout, which randomly drops out a column of pixels (feature map) of the image. The higher the layer, the more area of the element the dropout covers. By dropping out an entire column of pixels in the input image, the CNN may learn to rely on a variety of features for surface treatment evaluation, rather than one particular feature. Random vertical dropout may also prevent over training of the CNN, thus maintaining a desired accuracy level. Regardless of the techniques implemented, data augmentation allows the CNN to become more robust against variation in input images. This way, the CNN learns to extract important features under expected environmental variation caused by the way people take images, the conditions in which images are taken, and the hardware used to take images.

Preprocessing may also include normalization. As an example, global contrast normalization may be utilized to standardize the training images (and/or images of users). Similarly, the images may be masked with a fixed (or predetermined) size oval mask to minimize the influence of other features. This also forces the CNN to learn and not depend on only information in more fixed spatial location of the image.

During training, embodiments described herein may utilize mini-batch stochastic gradient descent (SGD) with Nesterov momentum (and/or other algorithms) to train the CNN. An example of utilizing a stochastic gradient descent is disclosed in U.S. Pat. No. 8,582,807. The objective function may include a mean square error. In some embodiments, about 10% of the training subject may be withheld. The training error and validation error on the withheld set may be monitored for training progress.

Once the CNN is trained, one or more of the CNN parameters may be fixed. As described in more detail below, a captured image may be forward propagated through the CNN to obtain a determined surface treatment regimen, which can optionally be displayed to the user, for example, on a mobile computing device.

The CNN may include an inputted image, one or more convolution layers C1, C2, one or more subsampling layers S1 and S2, a fully integrated layer, and an output. To begin an analysis or to train the CNN, an image is inputted into the CNN (e.g., the image of a user). The CNN may sample one or more portions of the image to create one or more feature maps in a first convolution layer C1. For example, the CNN may sample six portions of the image to create six features maps in the first convolution layer C1. Next, the CNN may subsample one or more portions of the feature map(s) in the first convolution layer C1 to create a first subsampling layer S1. In some instances, the subsampled portion of the feature map may be half the area of the feature map. For example, if a feature map comprises a sample area of 28×28 pixels from the image, the subsampled area may be 14×14 pixels. The CNN may perform one or more additional levels of sampling and subsampling to provide a second convolution layer C2 and a second subsampling layer S2. It is to be appreciated that the CNN may include any number of convolution layers and subsampling layers as desired. Upon completion of final subsampling layer, the CNN generates a fully connected layer F1, in which every neuron is connected to every other neuron. From the fully connected layer F1, the CNN can generate an output such as a predicted age or a heat map.

In some instances, at least some of the images and other data described herein may be stored as historical data for later use. As an example, tracking of user progress may be determined based on this historical data. Other analyses may also be performed on this historical data, depending on the embodiment.

In one embodiment, a CNN based model is used for detecting and tracking grooming implements 11 in a consumer video. The model utilizes multiple CNNs and other neural network components (such as a fully-connected network, or an RNN) to accomplish this task. The image data 23 in the form of consumer video is fed into the model as a series of image frames. Each image frame is first processed by a CNN to extract a set of feature maps (high-level features of the image). A second CNN, a Region Proposal Network, is used to propose a series of possible regions within the feature maps that might contain the grooming implement. The feature maps within the proposed regions are then extracted to be further proposed to a fully connected network to decide whether the proposed regions contain a grooming implement, refine the proposed regions positions, and map the coordinates of the proposed regions to the original image. The end result is that for each image frame, the model is able to decide whether a grooming implement exists, and if yes, the position of the grooming implement within the image. Concurrently, the consumer's face can also be located using various facial recognition algorithms including CNN or any other facial detector algorithm. It is possible to also have the face as part of the object detected in the described region proposal network. It is also possible to overlay a recurrent neural network to capture temporal information of the video. By combining location information of both grooming implement and consumer's face, the implement can respond accordingly to provide best grooming experience. In one embodiment, the operating parameters of the implement may be altered according to the manner in which the user is shaving, or otherwise grooming themselves or others. In one embodiment, the system may provide information to the user relating to the current as well as historic uses of the grooming implement and the target surface.

The image(s), as well as one or more outputs from the neural network may be passed to a database and aggregated with similar data from other users of the method. The aggregated data may be evaluated and categorized into clusters using known clustering methods. The instant user, surface and implement may then be associated with one or more of the now defined clustered populations based upon the data for the user, surface and implement. The association with particular cluster populations may then lead to the provision of cluster specific information to the user as part of the method. As an example, a user may be categorized according to age, ethnicity and gender and a comparison of the user's data with that of the cluster population for the same gender, age and ethnicity may provide insights of use to the practitioner when they are provided as part of the process.

In one embodiment, a method for treating a target surface 12 includes the steps of: automatically evaluating digital image data 23 of the target surface 12. The digital image data 23 (which may be a collection of images) may be provided to a machine learning classifier for evaluation. The collection of images may further include additional data associated with the content or context of the images. Data including audio, temperature, humidity or other environmental data captured contemporaneously with the images may also be provided to the classifier. The classifier may previously have been trained to identify the nature of the target surface 12 by presenting the classifier with training data including images of representative target surfaces either in isolation or together with other data as indicated above. The nature of the target surface 12 may include attributes including a categorization of the surface, such as skin, facial skin, teeth, fabrics, leather, plastics, wood, glass, ceramic, stone, or other hard or soft surfaces, as well as the current condition of the surface 12, the presence of facial hair, plaque, dirt, stains, and combinations thereof upon the target surface may be determined by the analysis of the surface via the images including the surface. The surface roughness or surface finish may also be determined.

The analysis of the at least one image may further identify or determine at least one available treatment implement. In one embodiment, the determination may comprise determining the presence of a hand-held treatment implement. In one embodiment, the determination may be made by matching content in the current images with images of suitable implements presented in the training data set. In one embodiment, the determination may be made by inference wherein particular implements are associated with certain surfaces according to previous definitions made available for the analysis. In this embodiment, a toothbrush may be associated with teeth, razors and implements with skin—body hair, scrub brushes with hard surfaces and so forth.

Further analysis of the at least one image and additional data may determine at least one surface treatment associated with the identified target surface in isolation or in conjunction with the identified treatment implement. This determination may be made utilizing the determination of the nature of the surface, the treatment implement, the practitioner, or combinations thereof. As an example, a grooming regimen may be determined as appropriate for a combination of a grooming implement and skin with hair. The analysis may then determine a use of the identified implement in the completion of the identified surface treatment.

Subsequent to the determinations, information analogous to the determined use may be provided to a user via a display system. Such information may include specific instructions regarding the handling and use of the implement in undertaking the treatment, the likely results of undertaking the treatment, the progression of the treatment as evaluated by the method over a series of treatments, the condition of the implement relative to performing the treatment and so forth. The information may be provided via digital display screen(s), by auditory cues from the implement or from distinct loudspeakers, or by visual cues such as indicator lights or other lighting changes in the treatment environment. In one embodiment, the step of providing information comprises providing cues analogous to the spatial interaction between the determined implement and the determined surface. In one embodiment, the step of providing information comprises providing information analogous to the temporal interaction of the determined implement and the determined surface. In one embodiment, the step of providing information comprises providing information through an alteration of a property of the determined implement.

In one embodiment, the information to be presented may be stored in a database and called in response to the output of the CNN. The presented information may be real-time information gathered during the treatment, information from the database and hybrid combinations of the two. As an example, a template display of upper and lower teeth may be presented to the user overlaid with real-time data illustrating which portions of the user's teeth have and have not been brushed during the current session. Data from the database illustrating trends of the user's brushing history may be presented.

In one embodiment, the step of providing information may include providing information associated with the determined use, product or implement as well as information associated with the user's social network. Social network information accessed using account information provided by the user may enable the presentation of information regarding similar treatments undertaken by members of the user's social network including similarities and differences between the treatment undertaken by the user and those treatments undertaken by other members of the user's social network. The social network information may also be used as an indicator of which social influencers are most likely to have an effect upon the user. This information may be used to select celebrity or social influencer how-to instructional content to present to the user as well as product review and testimonial information from the identified influencers or nearest analog to the identified influencers.

In one embodiment, the method further comprises the step of providing information regarding a treatment implement relevant to the determined surface or surface treatment, wherein the implement is not detected in the analysis of the data. As an example, analysis of the data may indicate the use of a grooming implement without the use of a complementary product which would improve or enhance the treatment activity. In this example, information regarding the missing product may be provided to the user.

In one embodiment, the step of providing information may include a gamification aspect. The information to be provided may be presented in the form of a game for the user. The game may include aspects such as point scoring, competition with others, and rules of play. As an example, use of an oral care implement such as a toothbrush may involve the presentation of the information related to the time spent brushing and the areas of the oral cavity I, including dental surfaces, tongue and gums, treated thus far as well as remaining to be treated, may be presented in the form of a game wherein the user must move the implement in a manner to clear objects from the display as a timer counts up or down. In this embodiment, the graphic elements presented for removal may coincide with the surfaces to be cleansed and may be removed from the display only after sufficient time has been spent by the user in treating/cleaning those surfaces.

In one embodiment, the method may further comprise the step of determining one or more properties of a treatment practitioner according to the evaluation of the at least one image. Properties including the practitioner gender, dominant hand, skin condition, beard condition, may be determined by analyzing the data and the context of the data together with other information regarding the user and the environment of the use. The determined properties of the practitioner may be used as inputs in determining what information to provide as the treatment activity is evaluated. Information specifically applicable to the user's gender, dominant hand, skin condition, beard condition, and combinations thereof may be provided.

In one embodiment, the information about the user may be combined with information about the product including brand, package quantity and quantity used for each treatment, to calculate product quantity remaining and thereby provide the user with an indication of when the current product is likely to run out as well as an indication of when the product should be replaced or re-ordered using the user's typical means of acquiring the product.

In one embodiment, the method further comprises the step of determining one or more environmental properties according to the evaluation of the one or more images together with at least one additional data source. As an example, the method may determine the location of the practitioner and the surface, the time of day, the lighting available at the location and other features of the local or external environment. The determined environmental properties may be used as input in determining what information to provide to the user as part of the method.

In one embodiment, the method may further comprise steps of: tracking an initial determined treatment of a determined target surface; providing information analogous to the determined treatment, tracking and evaluating subsequent treatments of the target surface; and altering subsequent provided information according to a machine learning evaluation of the tracked initial and subsequent determined treatments and previously provided information. As an example, a user may use the method to evaluate their shaving experience. Information may be provided to the use to enhance their shaving experience. Subsequent evaluations may indicate that portions of the previously provided information have been successfully followed or included in the shaving activity while other portions have not yet been added successfully. Subsequent to this determination, the provided information may be tailored to include only that information related to the portions which have not yet successfully been added to the treatment activity—in this example, shaving. Information types include shaving or treatment trends, ongoing treatment results—how well the user is shaving, what opportunities remain to improve their experience, and diagnostic information relating to the user's grooming implement as well as their shaving activities.

In one embodiment, the method may further comprise steps of: tracking an initial determined treatment of a determined target surface; tracking at least one subsequent determined treatment of the same determined treatment surface; using machine learning in evaluating the combination of tracked determined treatments of the determined target surface; and providing information analogous to the determined treatment of the determined target surface according to the evaluation of the combination of tracked determined treatments. The information provided may include indications of improvements to the grooming activities as well as outstanding opportunities for further improvements based upon a progression in the grooming results.

In this embodiment, the step of: machine learning in evaluating the combination of tracked determined treatments of the determined target surface, may comprise evaluating the practitioner in the combination using the environmental context of the treatment together with any information provided by the user.

In this embodiment, the step of: machine learning in evaluating the combination of tracked determined treatments of the determined target surface, may comprise evaluating the implement in the combination, the implement may be evaluated in terms of the manufacturer and model of the implement as well as the operational condition of the implement considered in terms of the implement's performance in completing the surface treatment. As an example, as the operating condition of the implement declines, the work necessary to complete the task will change.

In this embodiment, the step of: machine learning in evaluating the combination of tracked determined treatments of the determined target surface, may comprise evaluating the surface in the combination. The nature of the surface may be evaluated to provide an input to the determination of the information to be provided. Evaluation of a user's face may indicate a light or heavy growth of hair leading to the provision of different information dependent upon the facial hair present at the time of treatment.

In one embodiment, the method further comprises the step of altering a performance characteristic of the implement. In this embodiment, the driven frequency of the implement may be changed to alter the performance or to provide an auditory cue to the practitioner regarding the treatment of the surface using the implement.

A system for practicing the methods may include a network, which may be embodied as a wide area network (such as a mobile telephone network, a public switched telephone network, a satellite network, the internet, etc.), a local area network (such as wireless-fidelity, Wi-Max, ZigBee™, Bluetooth™, etc), and/or other forms of networking capabilities. Coupled to the network are a computing device, a remote computing device, a kiosk computing device, and a training computing device.

The computing device may be a mobile telephone, a tablet, a laptop, a personal digital assistant, an instrumented or smart mirror, and/or other computing device configured for capturing, storing, and/or transferring images such as digital photographs and video. Accordingly, the mobile computing device may include an image capture device such as a digital camera, including depth sensing cameras and/or may be configured to receive images from other devices. The mobile computing device may include a memory component, which stores image capture logic and interface logic. The memory component may include random access memory (such as SRAM, DRAM, etc.), read only memory (ROM), registers, and/or other forms of computing storage hardware.

Recent advances in a machine learning technique called deep learning have resulted in breakthrough performance in the realm of neural networks. Examples of deep learning neural networks include convolutional neural network (CNN) and recurrent neural network (RNN).

CNN utilize a plurality of layers inspired by the human visual cortex. A CNN consists of an input and an output layer, as well as multiple hidden layers. The hidden layers of a CNN typically consist of convolutional layers, pooling layers, fully connected layers and normalization layers. They have applications in a wide range of image and video applications, such as image classification, object detection, localization, segmentation, etc.

The CNN may be trained using predefined features and/or auto-learned features in a process called supervised learning. Supervised learning generally means that the CNN is trained by analyzing examples of images in which image classification/localization/detection/segmentation, etc. have been pre-defined. Depending on the accuracy that is desired, the number of training images may vary from a few images to a continuous input of images to provide for continuous training. Regardless, after training, the CNN learns key features for performing image related task.

After the CNN is trained, it may be used to generate an image classification, localization, detection, and/or segmentation related to operation of a personal grooming appliance. In some instances, the CNN can learn to identify facial/oral features, to recognize and localize grooming appliance devices, identify treatment area and treatment options, and to evaluate treatment results.

A recurrent neural network (RNN) is a class of deep learning neural network where connections between nodes form a directed graph along a sequence. This allows it to exhibit temporal dynamic behavior for a time sequence. RNNs use their internal state (memory) to process sequences of input data. This makes them applicable to tasks such as machine translation, speech recognition, video analysis, sound detection, and motion tracking, etc.

The RNN may be trained, similarly to CNN, using supervised learning. Supervised learning for RNN generally means the RNN is trained by analyzing examples of sequential data, such as text, speech, sounds, videos, sensor data streams in which translated words, meaning of sounds, action of videos, and corresponding physical measurement have been pre-defined. Depending on the accuracy that is desired, the number of training samples may vary from a few short snippets of data streams to a continuous input of data stream to provide for continuous training. Regardless, after training, the RNN learns key features for performing tasks involving sequential data.

After the RNN is trained, it may be used to analyze the data stream from cameras or physical sensors and provide additional information related to operation of a personal grooming appliance. In some instances, the RNN can learn to localize the grooming applicator, identify movement pattern of grooming applicator, and/or to assess the usage of the applicator.

Multiple type of deep learning neural networks are often used simultaneously to augment each other in order to achieve higher performance. In some instances, CNN and RNN can be used independently to analyze same or different streams of data, and the outputs from different neural network are jointly considered to drive user feedback. In other instances, a hybrid neural network architecture can be adopted—one hybrid neural network consists of both CNN and RNN branches or layers. In one type of hybrid network, intermediate results of CNN and RNN are jointly feed into additional layers of neural network to produce final output. In other type of hybrid networks, the output of one network (CNN, for example) is fed into additional layer of network (e.g. RNN) for further processing before final result is obtained.

In one embodiment, a CNN and RNN is used to analyze the image from an external camera and motion and pressure sensor from an electric shaver. The CNN first identifies option of treatment, e.g. recommended shaving technique based on facial area and natural of facial hair, the RNN then provides real-time tracking of brush motion to insure consumer follow the recommendations, and CNN is used in the end to provide post-shaving evaluation.

In another embodiment, a hybrid CNN/RNN model is used to provide highly accurate tooth localization during brushing. A toothbrush is equipped with both intra-oral camera and motion sensor and feed the hybrid network both vides stream and motion sensor stream. CNN and RNN components of the hybrid network analyze the video stream and motion sensor stream, respectively to provide intermediate results on localization of the brush head inside the mouth. The intermediate localization results are further processed by additional layers of neural network to yield an augmented localization of the brush-head as part of the feedback to user for better brushing results. Consequently, as will be appreciated, the internal sensor data $17_1$, $17_2$, $17_3$, ..., $17_n$ is not necessarily limited to motion sensor data, and the corresponding classifications $15_1$, $15_2$, $15_3$, ..., $15_n$ are not necessarily limited to motion patterns. For example, the internal sensor data $17_1$, $17_2$, $17_3$, ..., $17_n$ may comprise data from one or more pressure sensors, load sensors, temperature sensors, audio sensors/receivers, battery usage sensors, humidity sensors, bio-sensors and the like (such internal sensors of the appliance may also be referred to as "physical sensors"). Likewise, corresponding classifications $15_1$, $15_2$, $15_3$, ..., $15_n$ may be the result of classifying data from one or more of the sensors, or combinations of two or more of the sensors. Further, as will be discussed in further detail below, it is within the scope of the disclosure that the classifications $15_1$, $15_2$, $15_3$, ..., $15_n$ may comprise hybrid or augmented classifications based upon a classification of a combination of internal sensor data $17_1$, $17_2$, $17_3$, ..., $17_n$ and image data 22.

Figure 15:
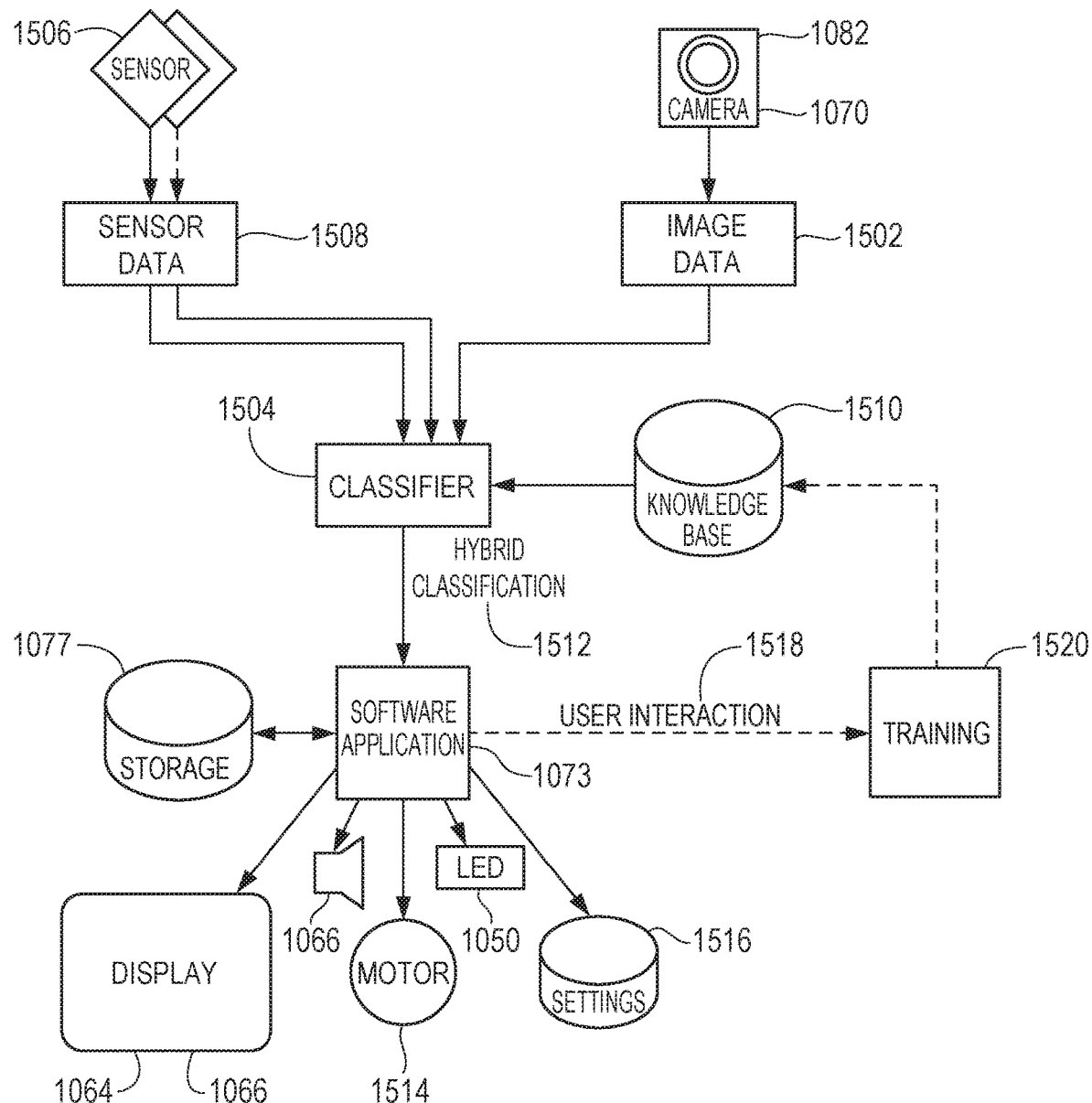
FIG. 15 is a block diagram representation of a networked system utilizing an augmented or hybrid machine learning classification according to an embodiment of the current disclosure.

FIG. 15 provides a schematic block diagram representation of an exemplary system according to an embodiment of the current disclosure utilizing such hybrid or augmented classifications. As shown in FIG. 15, a camera 1082/1070 is provided, which produces image data 1502 that is fed to a classifier 1504. Likewise, one or more sensors 1506 provide sensor data 1508 that are fed to the same classifier 1504. The classifier 1504 has access to a knowledge base 1510 that has been trained (and/or is being trained) based upon the various machine learning techniques described herein. The trained knowledge base 1510 is accessed by the classifier 1504 to classify the combination of image data 1502 and sensor data 1508 to provide a hybrid classification 1512 that is accessible by the software application 1073. The classifier 1504 may be any type of machine learning classifier and may utilize the neural networks (such as CNN and/or RNN) described herein, and the knowledge base 1510 comprises a trained (or training) set of potential classifications $15_1$, $15_2$, $15_3$, ..., $15_n$ and/or class members 101A, 101B, 102A, 102B, ..., nA, nB for matching/classifying against the input to the classifier(s).

For example, the classifier 1504 may be used to analyze an image from a camera 1070 associated with a smart phone or a smart mirror and the sensor data 1508 may include a pressure sensor data from an electric shaver. This hybrid classification 1512 produced by the classifier 1504 may provide a combination of position and pressure information for use by the application 1073 for real time tracking of shaver motion and pressure to ensure, for example, a customer is following a recommended shaving/treatment program. The classifier 1504, receiving the image data 1502 and further having received the combination of image data and sensor data 1502 and 1508 may also provide a post-shaving evaluation based upon the tracking classifications in combination with the post-shaving image classification. As another example, the classifier 1504 may be used to provide a highly accurate tooth localization during brushing. The toothbrush may be equipped with both an intra-oral camera 1082 and motion sensors 1506 and the classifier 1504 may receive the combination of the camera data 1502 and motion sensor data 1508 to provide a hybrid classification 1512, where the hybrid classification may use the combination of motion sensor and intra oral image information to provide an accurate localization of the brush head position inside the mouth. The software application 1073 may utilize this hybrid classification to generate feedback to the user for better brushing results.

This feedback may be provided, for example, to a display device 1064/1066, to a sound actuator device 1067 and/or to one or more LEDs 1050. The software application 1073 may also utilize the hybrid classification 1512 to adjust or modify the operation of the appliance. For example, the software application 1073 may adjust the operation of a motor 1514 present in the grooming appliance. As described herein, modifying the operation of the motor 1514 can be used, for example, to change the speed of an electronic toothbrush operation, to change the speed of an electronic shaving appliance operation, to change the angle of attack on a razor cartridge, to modify the speed or frequency of operation of a motor that controls the spinning or vibration of a brush or similar component of a household appliance and so forth. Likewise, the software application may utilize the hybrid classification information 1512 to change various settings 1516 for operating the grooming appliance and/or for operating the software application 1073. For example, depending upon the hybrid classification information 1512, device warning or notification settings may be altered (e.g., an over-pressure warning setting may be set at a different pressure depending upon the location of a shaving appliance with respect to a user's face or body-part).

As also shown in FIG. 15, the software application can utilize the hybrid classification information 1512 as part of a training process for further training the knowledge base 1510. For example, based upon how a user interacts with the software application 1073, that user interaction information 1518 can be used by a training process 1520 to further train the knowledge base.

Figure 16:
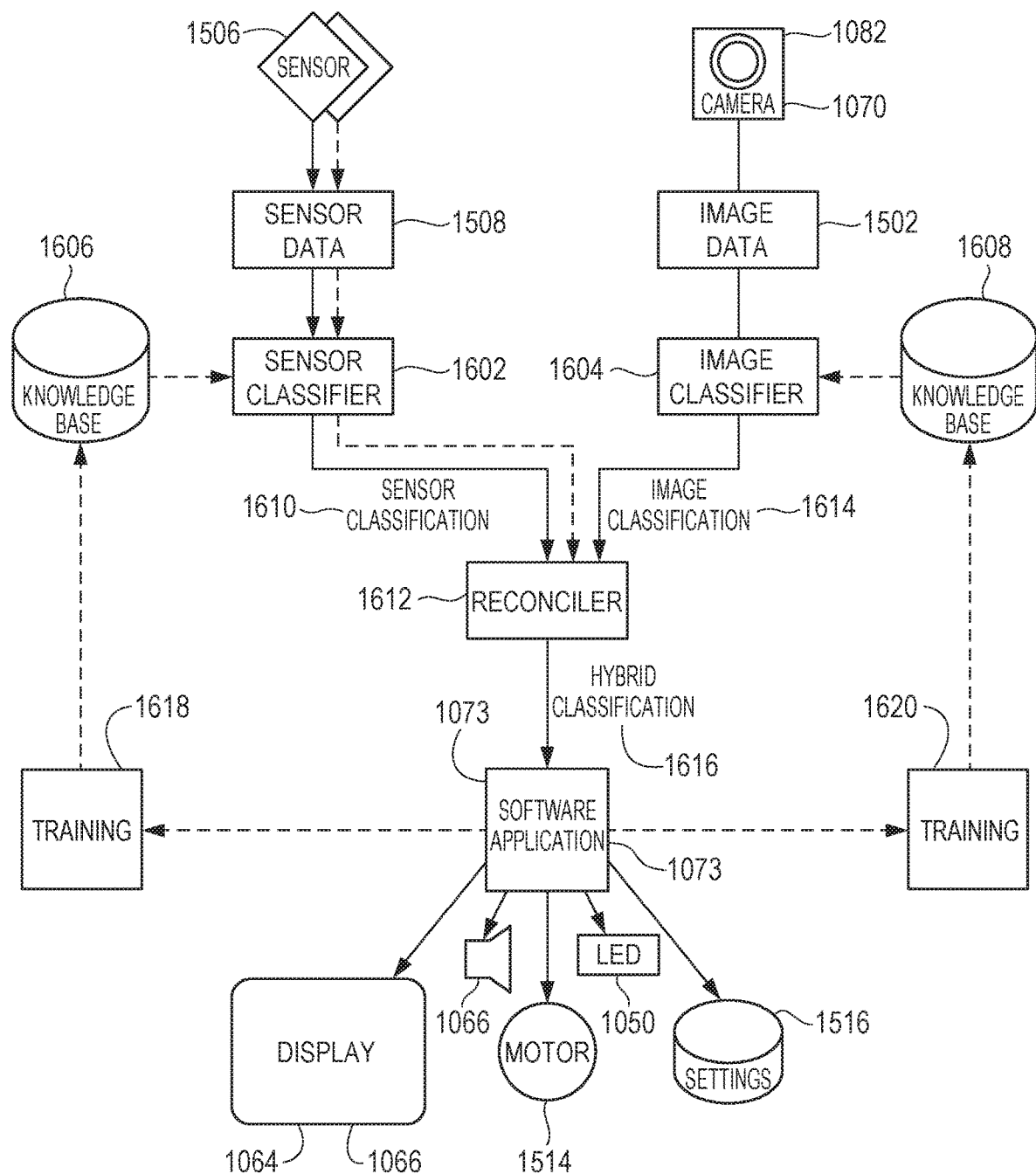
FIG. 16 is a block diagram representation of an alternate networked system utilizing an augmented or hybrid machine learning classification according to an embodiment of the current disclosure.

FIG. 16 provides a schematic block diagram representation of an exemplary system according to an embodiment of the current disclosure utilizing hybrid or augmented classifications generated in a different manner Referring now to FIG. 16, a schematic block diagram representation of an alternate system is provided. In this example system, the sensor data 1508 from the one or more sensors 1506 is fed to a sensor classifier 1602, while the image data 1502 received from the camera 1082/1070 is fed to a separate image classifier 1604. The sensor classifier classifies the sensor data based upon access to a trained knowledge base 1606 while the image classifier classifies the image data 1502 by accessing a train knowledge base 1608. The classifiers 1602/1604 may be any type of machine learning classifier and may utilize the neural networks (such as CNN and/or RNN) described herein, and the knowledge bases 1606/1608 comprise trained (or training) sets of potential classifications (such as potential classifications $15_1$, $15_2$, $15_3$, ..., $15_n$ and/or class members 101A, 101B, 102A, 102B, nA, nB) for matching/classifying against the input to the classifier(s) 1602/1604.

The sensor classifier 1602 generates one or more sensor classification(s) 1610 that are fed to a reconciler 1612, while the image classifier 1604 generates one or more image classification(s) 1614 that are also sent to the reconciler 1612. The reconciler 1612 receives the sensor classification 1610 and image classification 1614 (and, in some embodiments, associated confidence values) and generates a hybrid classification 1616 based upon a combination of the sensor classification(s) 1610 and image classification(s) 1614. The reconciler 1612 may utilize any of the neural network (such as CNN and/or RNN) classifications described herein or may utilized other forms of classification, such as utilizing a form of statistical classification, such as multinomial logistic regression, methods (or alternate classification methods) as known to those of ordinary skill. This hybrid classification 1616 information is then accessible by the software application 1073 for operation as described herein. Likewise, the knowledge base 1606 may be further trained by a training module 1618 while knowledge base 1608 may be further trained by a training module 1620. These training modules 1618/1620 may further train the respective knowledge bases 1606/1608 based upon user interaction information received from the software application 1073.

The reconciler 1612 may be a separate module or may be incorporated into the software application 1073. Additionally, the reconciler may not be present in all embodiments. For example, the sensor classification 1610 and image classification 1614 may be separately provided to the software application 1073 where the software application 1073 may not necessarily generate a hybrid classification 1616 based upon a combination of the sensor classification and image classification. For example, as described in the various use cases discussed herein, the software application 1073 may utilize an image classification initially to identify a surface condition of a user's body part (such as detecting the presence of plaque on a user's teeth or detecting whiskers on a user's face or legs) and then developing a treatment schedule based upon the image classification, where the treatment schedule may be provided to the user via the software application 1073. Subsequently following the development of the treatment program (such as recommendations as to how to brush your teeth, how to apply cosmetics, or how to shave), the software application may utilize the sensor classification information 1610 to follow the user's progress of treating the surface condition (such as brushing teeth, applying cosmetics, shaving a face or another body part). The software application 1073 can then be used to communicate to the user progress information based upon the sensor classification received.

It is also within the scope of the current disclosure that the treatment plan can be based solely upon the image classification 1614 while the progress information can be based upon the hybrid classification 1616. For example, the image classification 1614 may be used to determine a surface condition and, based upon the surface condition, the software application may establish a treatment plan. Thereafter, the software application may use the hybrid classification 1616 (which utilizes a combination of subsequent sensor classification(s) 1610 and subsequent image classification(s) 1614) to follow the progress of the treatment of the surface condition. Thereafter, based upon how the user is progressing with respect to the treatment plan established initially, the software application 1073 may communicate to the user how the user is performing with respect to the treatment plan, may modify the treatment plan or may correct the initial image classification (indicating that the initial image classification may have detected the incorrect surface condition) and develop a new treatment plan based upon the revised indication.

The example system shown in FIGS. 15 and 16 can be used for many use cases including, but not limited to grooming appliance and household appliance use cases. Only a number of potential use cases will be discussed herein, but it will be appreciated that many more are envisioned and within the scope of the current disclosure.

In a first use case example, the image data 1502 may be utilized to indicate the lubrication product (i.e., shaving gel) being used (such as by brand or type); and may also indicate the facial hair area being shaved, the direction of the shave, and/or the delay time between applying the shaving lubricant and the act of shaving. In the same example, the sensor data 1508 may be MEMS (microelectromechanical systems) motion information, speed information, pressure information of a razor on the face, and/or positional information. The hybrid classification 1512/1616, in this example, may be used by the software application 1073 for various benefits. For example, as razors wear down, efficacy decreases and the consumer typically speeds up strokes and applies additional pressure to compensate. The software application 1073 can detect subtle changes in the user's routine (shave metrics) and changes in the components of the shave (such as the shave gel type) to recommend to the user changes in the routine and/or components to ensure a successful shaving experience. Alternatively, the software application can use the hybrid classification 1512/1616 to detect a need for a different angle of attack of the shaving cartridge or a different level of resistance in the pivoting of the shaving cartridge and modify operation of a component 1514 and/or modify a setting 1516 of the appliance accordingly.

In another exemplary use case, the image data 1502 may be an image of a user's face, while the sensor data 1508 may include MEMS sensor information pertaining to a location of the grooming appliance with respect to the user's face. The software application 1073 may analyze the image classification 1614 or the hybrid classification 1512/1616 to determine an emotional response of the user while using a grooming appliance (such as a shaving appliance, dental appliance or cosmetic applicator); and, likewise, use the positional information present in the sensor classification 1610 or hybrid classification 1512/1616 to determine where the grooming appliance was located (and/or how the grooming appliance was being used) at the time of the experience of the emotional reaction. The application 1073 may then use that combination of information to provide feedback to the user or to modify operation of a component 1514 and/or modify a setting 1516 of the appliance. As an example, if the user shows a negative emotion shaving his neck, and the hybrid classification 1512/1616 indicates that a certain pressure and shaving direction was being used at that time, the application 1073 may suggest to the user a different way to shave his neck the next time.

In another example use case, the image data 1502 may be used to provide pre- and/or post-shave information while the sensor data 1508 may include location information, speed of movement information, and/or pressure information of a shaving device. Using this combination of information as described above, the application 1073 can analyze the images before shaving to determine direction of whiskers and a best treatment approach to obtain a close shave. Thereafter, data from the sensor information 1508 and/or hybrid classification 1512/1616 may indicate how the shave was performed as compared to the recommendations. The post-shaving image information may then be analyzed and the application may refine its guidance for a better shave the next time the user attempts to use the shaving appliance. For example, if the post shave images show irritation and the guidance was followed, the application may offer post shave options (such as shave ball) or recommend pre shave routines (such as using a warm towel, a new blade, and/or a different shaving foam) to help minimize issues. The application 1073 may also tag the consumer for future product development follow-up (for example, if there is a tendency for the consumer to get in-grown hairs after shaving, the application 1073 may offer marketing information to the user different products that may be utilized to avoid in-grown hairs in the future).

In a next example use case, the combination of image classification and sensor classifications may be utilized in a marketing context. For example, the image data 1502 may provide, during brushing, the products used by the user (power brush vs. manual, toothbrush, toothpaste type, mouthwash, floss, etc.) while the sensor data 1508 may provide location, speed and pressure information during the brushing activity. The application 1073, leveraging the hybrid classification 1512/1616 and contextual data (such as the identity of the user, the age of the user, the ethnicity of the user, user's habits, products present, etc.) may cross-sell consumers to different products. For example, a consumer who is brushing with a manual toothbrush and uses sensitivity toothpaste may be receptive to messaging, coupons, samples of a power brush with soft bristles and/or a different toothpaste used to minimize future sensitivity issues.

In another use case, the image data 1502 may be used by the software application 1073 as classifying a skin age analysis before product use, and may also be utilized during use for locational information. The sensor data 1508 may be various performance conditions of the beauty product applicator being used, such as speed of use, pressure and the like. Then, based upon this combination of information, the application 1073 may recommend a cosmetic and an application technique to the user through the application 1073 to maximize performance. The application 1073 may leverage data from the sensor data from the applicator device to understand how (pressure and motion) the product is being applied, patted, rubbed, dotted). The application 1073 may track and coach on technique to encourage adhering to the guidance using the application.

In another use case example, a camera 1082 located on a leading end of a dental appliance may be used to identify the presence and locations of plaque on a user's teeth. Based upon this identification of the location and presence of plaque on the user's teeth, the software application 1073 may thereafter generate a treatment plan which will be communicated to the user. This treatment plan may provide a recommendation for how to brush the user's teeth using the manual or electronic toothbrush and may also guide the user to the various tooth locations in real time during brushing (such as via a display 1066 on a smart mirror device). For example, while the user is brushing before a smart mirror device, there may be an animated display on the corner of the device showing to the user where the user has brushed and where the user has not brushed and where the presence of plaque may still be indicated so that the user will know what parts of the user's mouth to complete brushing before finishing the brushing activity. Consequently, during brushing, the hybrid classification 1616/1512 may be a hybrid combination of positional data from the sensor data 1508 and image data 1502 to provide to the application 1073 progress information of how the user is doing with the brushing activity.

In a similar example, an external camera 1070 located on a computerized smart phone or smart mirror 1080 may be used to analyze a target such as a room, a floor, a window and the like and the application 1073 may be used to determine the state of the target. Using this information, the software application 1073 may set goals or a treatment plan for using the grooming appliance or household appliance for treating the target. Thereafter, once implemented, the software application 1073 may utilize the sensor information 1602 (which may include motion sensor data) or the hybrid classification 1512/1616 to monitor the use of the appliance with respect to the target to determine whether or not the goals are of treating the state of the target are accomplished.

In another example, the image classifier 1604 may be used to determine the identification of the target and the appliance being used with respect to the target (a user's face and a shaving appliance). Thereafter, the sensor classification 1610 or the hybrid classification 1512/1616 may be used to determine how the grooming appliance is engaging with the target. The software application 1073 may utilize a hybrid classification 1512/1616 to obtain a refined determination of how the implement and the target are interacting and based upon this hybrid classification information may provide user feedback in real-time or after use.

As some additional examples when operating as a toothbrush, the application can utilize the hybrid classification 1512/1616 to determine when a toothbrush is outside of a user's mouth and based upon this determination may disable or turn off the device, or at least disable or turn off the motor 1514 operating the motorized toothbrush. As another example, based upon this hybrid classification information 1512/1616 the software application 1073 may change the color of a multi-color LED 1050 (such as a smart ring) based upon the software application utilizing the hybrid classification 1512/1616 to determine the identity or other characteristic of the user. In another example, the hybrid classification 1512/1616 may be used to detect a brush head type of the grooming appliance and then be used to determine whether or not to change the speed setting 1516 of the brush (a detection of a soft bristle may result in setting a default speed to "gentle"). As another example, the hybrid classification 1512/1616 may be used to detect brush position with respect to the user and then the software application 1073 may automatically adjust the speed of the brush by modifying operation of the motor 1514 or by modifying a speed setting 1516 (for example, when the hybrid classification indicates that the brush is positioned on a tongue of the user, the operation of the device is modified based upon tongue cleaning settings). As another example, the hybrid classification 1512/1616 may be used to determine the location of a shaving appliance with respect to a user's skin and then adjust a pressure warning setting depending upon the area of the grooming device with respect to the user (for example, if the grooming device is on a position of the skin where sensitivity is not likely, the settings 1516 may be modified so that a pressure warning produced by speaker 1066 will only be activated at a higher level of pressure is sensed as compared to a lower level if the hybrid classification indicates that the shaving device is located in an area of high sensitivity). As another example, the hybrid classification 1512/1616 can be used to determine how long the grooming appliance has been used since a grooming implement, such as a razor cartridge or toothbrush head, has been changed. Consequently, the application 1073 may use this information to advise the user that it's time to change the brush head of a toothbrush or a shaving cartridge on a shaver if the appliance has been used for a longer than a recommended replacement schedule.

As discussed above, the software application 1073 can use the hybrid classifications 1512/1616 to adjust the operation of the grooming appliance or household appliance in many different ways. For example, the software application 1073 may turn on or off the grooming appliance or implements contained in the appliance; may adjust the speed of the implements of the grooming/household appliance; may adjust the pressure settings permitted before warning of the grooming/household appliance; may activate lights, LEDs, colors, etc. based upon the operation of the grooming appliance/household appliance; may adjust the operation of the appliance for maintenance related issues such as compensating for lack of maintenance (old shaving foils, old brushes, etc.); may provide feedback to the user suggesting replacement of an implement, such as recommending replacing a worn out brush or shaving cartridge, etc.; may adjust operational settings, such as angle of attack for a shaving device based on facial location; and may adjust the stiffness or maneuverability of the appliance implements (such as the pivoting stiffness of a razor cartridge).

As discussed above, the application 1073 may provide various forms of feedback to the user of the appliance. Such feedback may be visual (such as provided through a networked user interface device 1080 such as a smart phone, tablet, personal assistant, or smart mirror device), audio (spoken, sounds, etc) from the appliance itself or from some other device such as a personal assistant device, haptic feedback from the appliance or from some other source and the like. Of course, the feedback may be any combination of visual, audio and haptic. For example, the feedback may be in the form of an animated video presented on the device 1080 before, during and/or after use of the appliance.

The training modules 1520/1618/1620 may train the classifiers based upon user interaction with the application 1073 as discussed above. But the training may also be based upon an individual's use of the appliance (e.g., left-handed vs. right-handed). The training may also be a crowd-based training where multiple users train the classifiers based on overall habits and usage.

The application 1073 may also train the classifiers based upon how the user follows (or fails to follow) treatment advice or other feedback.

Embodiments disclosed herein may use the augmented or hybrid classification 1512/1616 to determine the relative position/location of a target surface and the nature of the target surface of a subject. An embodiment provides an appliance, comprising a sensor equipped appliance for the acquisition and transmission of the sensor data 1508 and for receiving and processing of the sensor data to determine the relative position of a target surface and the nature of the target surface.

The assessment of a target surface including the acquisition and processing of at least one digital image 1502 of the target surface and its nature, consisting of information of oral conditions, issues and diseases including, but not only limited to plaque, stain, calculus, discoloration, early and late stages of caries, white spot lesion, fluorosis, demineralization, gingivitis, bleeding, gingival recession, periodontitis, fistula, gingival abrasion, aphthous, other lesions of mucosa and structure and cleanliness of tongue. The assessment of a target surface includes also the determination of sound teeth, gums, mucosa and tongue, as well as the determination of missing teeth, teeth alignment and artificial materials like dental implants, dentures, crowns, inlays, fillings, brackets and other tooth position correcting appliances. The assessment of a target surface can also be part of a determination of an oral health index generated via intra-oral-cameras and smart analysis systems based on, but not limited to, machine learning, deep learning and artificial intelligence.

The assessment results from position, target surface and its nature (data) analyzed over time help to drive the robustness of the analysis for endpoints like plaque, gingivitis and other endpoints listed above. For the acquisition of data, the sensor equipped device may use sensors such as, but not limited to, optical sensors, cameras, bio-sensors and Inertia Measurement Units. For the acquisition of data, the sensor equipped device may use additional light sources to allow to detect endpoints like, but not limited to, plaque and to optimize the environmental conditions for the sensors. The sensor equipped device may use preprocessing or filtering methods to alter the sensor data before transmission. For processing the acquired position, target surface and nature of target surface (data), the software within the system may use mathematical methods such as but not limited to statistical analysis, machine learning, deep learning, artificial intelligence, etc such as those described herein.

In an embodiment, the device may contain software for operation of the device and for processing and displaying of the position, the target surface and the nature of the target surface (data). In an embodiment, the position, the target surface and the nature of the target surface is displayed either in real-time/live during the data acquisition or after data processing. In this setup, the target surface and the nature of the target surface data can be shown solitary or can be combined with the position data to be projected to a real or abstract model.

With respect to the embodiments of FIGS. 15 and 16, the bio-sensors may be utilized in place of the cameras 1082/1070 so that the augmented or hybrid classifications 1512/1616 may be based upon a classification of a combination of bio-sensor data and internal sensor data 1508. In an example, the system could detect gingivitis on the upper buccal dental zone. This information is transferred to an Oral Care cleaning system so that, when brushing in the specified zone, the application 1073 changes the brushing mode setting 1516 to "sensitive" and the "pressure threshold" settings 1516 will be set lower.

As another modified use case, a diagnosis of a medical condition combined with the location of that condition may also result in a modification of the operation of the appliance in that location. For example, an operation of an electric toothbrush may be automatically adjusted to a "sensitive" mode of operation when the hybrid classification 1512/1616 determines that the toothbrush is in a location of the mouth where gingivitis has been (or is being) diagnosed.

It will be apparent that changes or modifications may be made to the exemplary embodiments without departing from the scope as claimed below. Furthermore, it is also not necessary that the any objects or advantages discussed herein be present to fall within the scope since many advantages may be present without necessarily being disclosed herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or patent publication, is hereby incorporated herein by reference in its entirety unless expressly excluded or otherwise limited. The citation of any document is not an admission that it is prior art with respect to any document disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method for operating a household cleaning appliance, comprising:
   providing a household cleaning appliance including,
      a powered and electronically controlled cleaning implement, and
      at least one physical sensor taken from a group consisting of: an orientation sensor, an acceleration sensor, an inertial sensor, a global positioning sensor, a pressure sensor, a load sensor, audio sensor, humidity sensor, and a temperature sensor;
   providing a camera associated with the household cleaning appliance;
   deriving an augmented classification using one or more classifiers classifying the physical sensor data and the image data;
   modifying operation of the cleaning implement based upon the augmented classification; and,
   wherein the augmented classification pertains, at least in part, to whether or not the cleaning implement is being implemented, and the step of modifying operation updates a maintenance setting based upon an amount of time that the cleaning implement is being implemented.

2. The method of claim 1, wherein the camera is located on the household cleaning appliance.

3. The method of claim 1, wherein:
   the household cleaning appliance further includes a computer network interface transmitting and receiving data over a computer network;
   the camera is located on a computerized device that includes computer network interface at least transmitting image data over the computer network.

4. The method of claim 3, wherein the operation modifying step is further based upon a treatment plan implemented by a software application operating, at least in part, on the computerized device.

5. The method of claim 4, wherein the treatment plan is customized for a user of the household cleaning appliance.

6. The method of claim 4, wherein the augmented classification is reconciled against the treatment plan to determine treatment progress with respect to the treatment plan.

7. The method of claim 4, wherein the augmented classification is used, at least in part, to establish the treatment plan.

8. The method of claim 1, wherein the step of deriving the augmented classification is performed by a single classifier.

9. The method of claim 1, further comprising:
   classifying sensor data received from the physical sensor using a trained machine learning classifier to generate a physical classification; and
   classifying image data received from the camera using a trained machine learning classifier to generate an image classification;
   wherein the step of deriving the augmented classification is based upon the combination of the physical classification and the image classification.

10. The method of claim 1, wherein the augmented classification pertains, at least in part, to the position of the cleaning implement with respect to a target surface, and the step of modifying operation modifies operation of the cleaning implement, based at least in part, upon the position of the of the cleaning implement with respect to the target surface as indicated, at least in part, by the augmented classification.

11. The method of claim 1, wherein:
   the augmented classification further includes a surface condition of the target surface; and
   the step of modifying operation adjusts a performance setting of the cleaning implement based upon a surface condition at the position of the cleaning implement with respect to the target surface as indicated, at least in part, by the augmented classification.

12. A method for operating a household cleaning appliance, comprising:
   providing a household cleaning appliance including at least one physical sensor taken from a group consisting of: an orientation sensor, an acceleration sensor, an inertial sensor, a global positioning sensor, a pressure sensor, and a load sensor, audio sensor, humidity sensor, and a temperature sensor;
   providing a camera associated with the household cleaning appliance;
   classifying data received from the physical sensor and from the camera using at least one trained machine learning classifier to generate an augmented classification;
   providing user feedback information based upon the augmented classification;
   wherein the augmented classification pertains to a combination of a first state pertaining to a position of the household cleaning appliance with respect to a target surface and also pertains to a second state that is different than the first state; and, wherein the second state pertains to an identity of a user or the identity of the household cleaning appliance.

13. The method of claim 12, wherein the first state also pertains to a direction of movement of the household cleaning appliance.

14. The method of claim 12, wherein the step of generating the augmented classification is performed by a single classifier.

15. The method of claim 12, further comprising:
classifying sensor data received from the physical sensor using a trained machine learning classifier to generate a physical classification; and
classifying image data received from the camera using a trained machine learning classifier to generate an image classification;
wherein the step of generating the augmented classification is based upon the combination of the physical classification and the image classification.

* * * * *